US006777431B2

(12) United States Patent
Siev et al.

(10) Patent No.: US 6,777,431 B2
(45) Date of Patent: Aug. 17, 2004

(54) NON-CONVALENT THROMBIN INHIBITORS

(75) Inventors: Daniel Vanna Siev, San Diego, CA (US); Joseph Edward Semple, San Diego, CA (US); Mallareddy Komandla, San Diego, CA (US); John Eugene Reiner, San Diego, CA (US); Scott Jeffrey Kemp, San Diego, CA (US)

(73) Assignee: Corvas International, Inc., San Diego, CA (US)

( * ) Notice: Subject to any disclaimer, the term of this patent is extended or adjusted under 35 U.S.C. 154(b) by 0 days.

(21) Appl. No.: 09/905,644

(22) Filed: Jul. 13, 2001

(65) Prior Publication Data

US 2003/0092679 A1 May 15, 2003

(51) Int. Cl.[7] .................. C07D 213/63; C07D 403/06; C07D 413/06; A61K 31/44; A61P 7/02
(52) U.S. Cl. ...................... 514/345; 546/294; 544/111; 514/231.5
(58) Field of Search .................. 546/294, 297; 514/345, 231.5, 348; 544/111

(56) References Cited

U.S. PATENT DOCUMENTS

| | | | |
|---|---|---|---|
| 5,371,072 A | 12/1994 | Webb et al. | 514/18 |
| 5,492,895 A | 2/1996 | Vlasuk et al. | 514/18 |
| 5,534,498 A | 7/1996 | Brunck et al. | 514/19 |
| 5,597,804 A | 1/1997 | Webb et al. | 514/18 |
| 5,637,599 A | 6/1997 | Levy et al. | 514/326 |
| 5,646,165 A | 7/1997 | Abelman et al. | 514/315 |
| 5,656,600 A | 8/1997 | Abelman et al. | 514/13 |
| 5,656,645 A | 8/1997 | Tamura et al. | 514/349 |
| 5,696,231 A | 12/1997 | Abelman et al. | 530/331 |
| 5,721,214 A | 2/1998 | Marlowe et al. | 514/18 |

FOREIGN PATENT DOCUMENTS

| | | |
|---|---|---|
| EP | 0 293 881 B1 | 12/1988 |
| EP | 0 363 284 B1 | 4/1990 |
| EP | 0 526 877 A2 | 2/1993 |
| WO | 94/13693 | 6/1994 |
| WO | 95/35311 | 12/1995 |
| WO | 95/35313 | 12/1995 |
| WO | 96/19493 | 6/1996 |
| WO | WO-9701338 | * 1/1997 |

OTHER PUBLICATIONS

Rauch et al. Ann. Intern. Med. 134(3): 224–238,2001.*
Van Aken et al., Clin. Appl. Thromb. Hemost. 7(3): 195–204, 2001.*
Bajusz, S., et al., Highly Active and Selective Anticoagulants: D–Phe–Pro–Arg–H, a Free Tripeptide Aldehyde Prone to Spontaneous Inactivation, and Its Stable N–Methyl Derivative, D–MePhe–Pro–Arg–H, *J. Med. Chem.* 33:1729–1735 (1990).
Bajusz, S., et al., Inactivation of Thrombin and Trypsin by Tripeptide Aldehydes, *Int. J. Peptide Protein Res.,* 12:217–221 (1978).
Bajusz, S., Interaction of Trypsin–Like Enzymes With Small Inhibitors, *Symposia Biologica Hungarica,* 25:277–298 (1984).
Fujii, S., et al., New Synthetic Inhibitors of C1⊤, C1 Esterase, Thrombin, Plasmin, Kallikrein and Trypsin, *Biochimica et Biophysica Acta,* 661:342–345 (1981).
Geratz, J.D., et al., Novel Bis(benzamidino) Compounds with an Aromatic Central Link. Inhibitors of Thrombin, Pancreatic Kallikrein,[1] Trypsin, and Complement, *Journal of Medicinal Chemistry,* 19:634–639 (1976).
Geratz, J.D., et al., Diamidion–a,ω–diphenoxyalkane, Structure–Activity Relationships for the Inhibition of Thrombin, Pancreatic Kallikrein, and Trypsin, *Journal of Medicinal Chemistry,* 16:970–975 (1973).
Geratz, J.D., Structure–Activity Relationships for the Inhibition of Plasmin and Plasminogen Activation by Aromatic Diamidines and a Study of the Effect of Plasma Proteins on the Inhibition Process, *Thrombosis et Diathesis Haemorrhagica,* 29:154–167 (1973).
Hauptmann, J., et al., Zur Wirkung von aromatischen Bisamidinen auf Blutgerinnungs– und Fibrinolysevorgänge, *Acta Biologica et Medica Germanica,* 35:635–644 (1976).
Hitomi, Y., et al., Inhibitory Effect of a New Synthetic Protease Inhibitor (FUT–175) on the Coagulation System, *Haemostasis,* 15:164–168 (1985).
Kelly, A.B., et al., Relative Antithrombotic Potencies and Hemostatic Risks of Reversible D–Phe–Pro–Arg (D–FPR) Antithrombin Derivatives, *Thrombosis and Haemostasis,* 65:736 (Abstract #257).
Kettner, C., et al., Inactivation of Trypsin–Like Enzymes with Peptides of Arginine Chloromethyl Ketone, *Methods in Enzymology,* 80:826–842 (1987).
Kettner, C., et al., The Selective Inhibitors of Thrombin by Peptides of Boroarginine, Journal of Biological Chemistry, 265(30):18289–18297 (1990).
Ohno, H., et al., FOY: (Ethyl p–(6–quanidinohexanoyloxy) benzoate methanesulfonate As a Serine Proteinase Inhibitor, I. Inhibition of Thrombin and Factor Xa in vitro, *Thrombosis Research,* 19:579–588 (1980).
Walsmann, et al., Synthetische Inhibitoren der Serinproteinasen[1], *Acta Biologica et Medica Germanica,* 35:K1–K8 (1976).

* cited by examiner

Primary Examiner—Venkataraman Balasubramanian
(74) *Attorney, Agent, or Firm*—Suzanne L. Biggs; Pillsbury Winthrop LLP

(57) ABSTRACT

The present invention provides compounds which have a pyrazinone or pyridinone ring at P3 and an optionally substituted heteroaryl group at P1. These compounds have biological activity as active and potent inhibitors of thrombin. Their pharmaceutically acceptable salts, pharmaceutical compositions thereof and methods of using these compounds and pharmaceutical compositions comprising these compounds as therapeutic agents for treatment of disease states in mammals which are characterized by abnormal thrombosis are also described.

49 Claims, 3 Drawing Sheets

| COMPOUND | STRUCTURE |
|---|---|
| A | 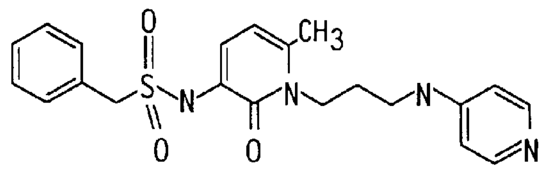 |
| B | 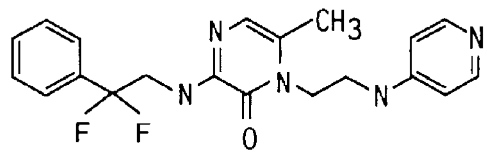 |
| C | 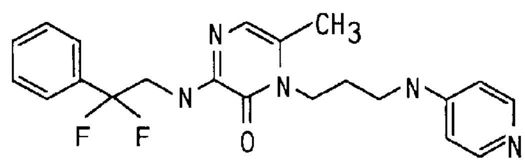 |
| D | 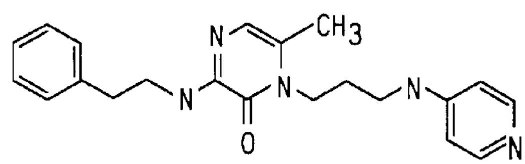 |
| E | 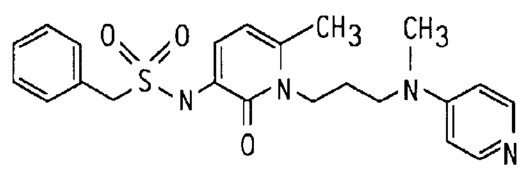 |
| F | 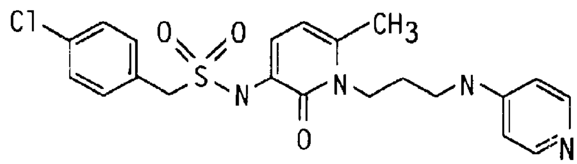 |

FIG. 1A

| COMPOUND | STRUCTURE |
|---|---|
| G | 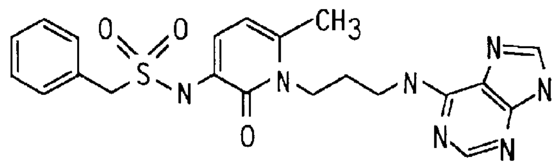 |
| H | 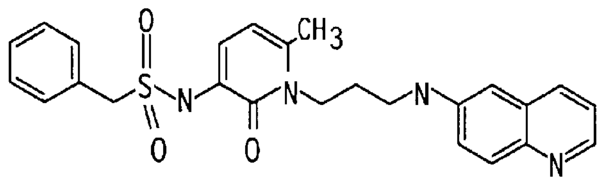 |
| I | 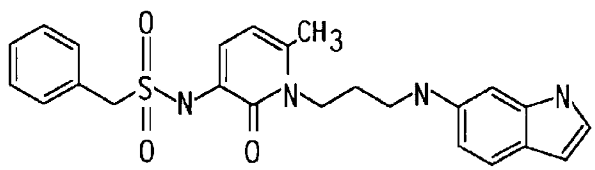 |
| J | 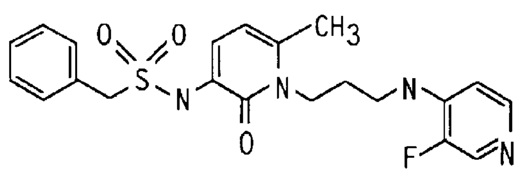 |
| K | 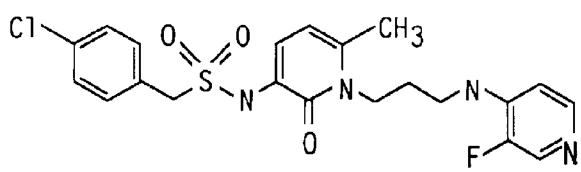 |
| L | 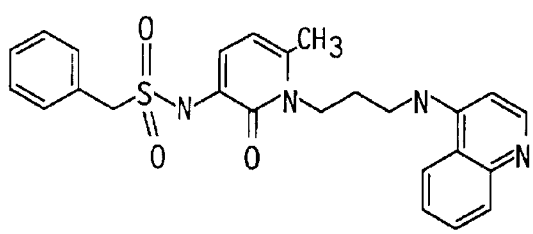 |

FIG. 1B

| COMPOUND | STRUCTURE |
|---|---|
| M | 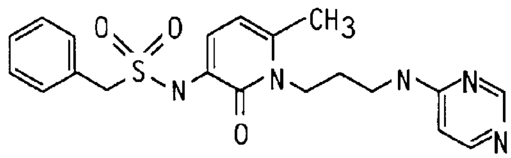 |
| N | 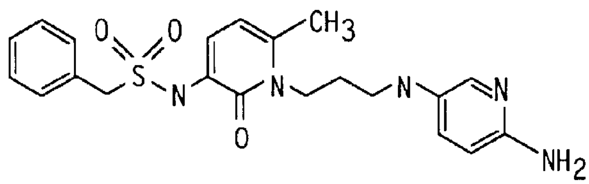 |
| O | 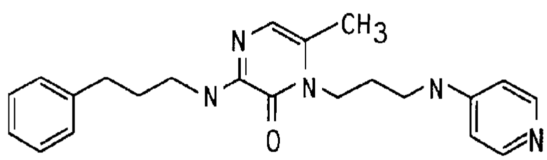 |
| P | 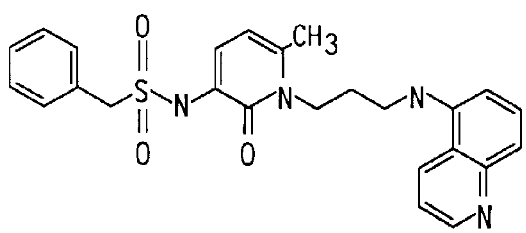 |
| Q | 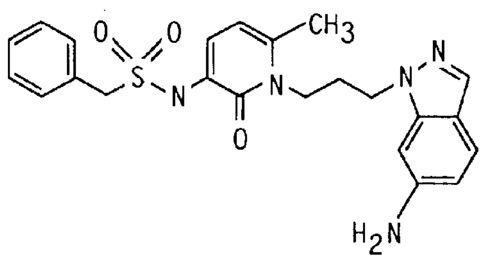 |
| R | 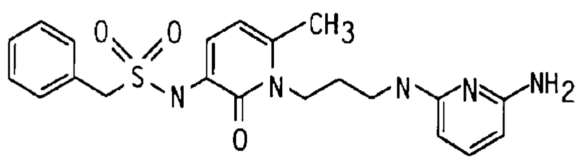 |

NON-CONVALENT THROMBIN INHIBITORS

TECHNICAL FIELDS

In one aspect, the present invention relates to compounds which are potent inhibitors of thrombin. In another aspect, the present invention relates to novel peptide analogs, their pharmaceutically acceptable salts, and pharmaceutically acceptable compositions thereof, which are useful as potent inhibitors of blood coagulation in vitro and in vivo in mammals. In yet another aspect, the invention relates to methods of using these inhibitors as therapeutic agents for disease states in mammals characterized by abnormal thrombosis. In a further aspect, the present invention relates to methods of using these inhibitors as in vitro diagnostic agents.

BACKGROUND AND INTRODUCTION TO THE INVENTION

Normal hemostasis is the result of a complex balance between the processes of clot formation (blood coagulation) and clot dissolution (fibrinolysis). The complex interactions between blood cells, specific plasma proteins and the vascular surface, maintain the fluidity of blood unless injury occurs. Damage to the endothelial barrier lining the vascular wall exposes underlying tissue to these blood components. This in turn triggers a series of biochemical reactions altering the hemostatic balance in favor of blood coagulation which can either result in the desired formation of a hemostatic plug stemming the loss of blood or the undesirable formation of an occlusive intravascular thrombus resulting in reduced or complete lack of blood flow to the affected organ.

The blood coagulation response is the culmination of a series of amplified reactions in which several specific zymogens of serine proteases in plasma are activated by limited proteolysis. Nemerson, Y. and Nossel, H. L., Ann. Rev. Med., 33: 479 (1982). This series of reactions results in the formation of an insoluble fibrin matrix composed of fibrin and cellular components which is required for the stabilization of the primary hemostatic plug or thrombus. The initiation and propagation of the proteolytic activation reactions occurs through a series of amplified pathways which are localized to membranous surfaces at the site of vascular injury (Mann, K. G., Nesheim, M. E., Church, W. R., Haley, P. and Krishnaswamy, S. (1990) Blood 76: 1–16; and Lawson, J. H., Kalafatis, M., Stram, S., and Mann, K. G. (1994) J. Biol. Chem. 269: 23357–23366).

These pathways are highly inter-dependent and converge in the formation of the serine protease, Factor Xa. Factor Xa catalyzes the penultimate step in the blood coagulation cascade which is the formation of the serine protease thrombin. This step occurs following the assembly of the prothrombinase complex which is composed of factor Xa, the non-enzymatic co-factor Va, and the substrate prothrombin assembled on the surface of adhered, activated platelets or systemically circulating membranous microparticles.

Proteolytic activation of zymogen factor X to its catalytically active form, factor Xa, can occur by either the intrinsic or extrinsic coagulation pathways.

The intrinsic pathway is referred to as "intrinsic" because everything needed for clotting is in the blood. Saito, H., "Normal Hemostatic mechanisms", *Disorders of Hemostasis*, pp. 27–29, Grune & Stratton, Inc. (O. D. Ratnoff, M. D. and C. D. Forbes, M. D. edit. 1984). This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X which subsequently results in clot formation.

The extrinsic pathway is referred to as "extrinsic" because the tissue factor which binds to and facilitates the activation of factor VII comes from outside the blood. Saito, id. The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

The formation of thrombin is catalyzed by factor Xa following the assembly of the catalytic prothrombinase complex as reviewed by Mann, K. G. et al., "Surface-Dependent Reactions of the Vitamin K-Dependent Enzyme Complexes," *Blood*, 76:1–16 (1990). This complex is composed of factor Xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", *J. Clin. Invest.*, 71:1383–1391 (1983). In addition, sequestration of factor Xa in the prothrombinase complex also renders it resistant to inhibition by exogenous heparin therapy which also requires antithrombin III to elicit its anticoagulant effect.

Thrombin is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., *Arch. Biochem. Biophys.*, 105:58 (1964). Beyond its direct role in the formation and stabilization of fibrin rich clots, the enzyme has been reported to have profound bioregulatory effects on a number of cellular components within the vasculature and blood. Shuman, M. A., *Ann. NY Acad. Sci.*, 405:349 (1986).

It is believed that thrombin is the most potent agonist of platelet activation, and it has been demonstrated to be the primary pathophysiologic-mediator of platelet-dependent arterial thrombus formation. Edit, J. F. et al., *J. Clin. Invest.*, 84:18 (1989). Thrombin-mediated platelet activation leads to ligand-induced inter-platelet aggregation principally due to the bivalent interactions between adhesive ligands such as fibrinogen and fibronectin with platelet integrin receptors such as glycoprotein IIb/IIIa which assume their active conformation following thrombin activation. Berndt, M. C. and Phillips, D. R., *Platelets in Biology and Pathology*, pp. 43–74, Elsevier/North Holland Biomedical Press (Gordon, J. L. edit. 1981). Thrombin-activated platelets can also support further thrombin production through the assembly of new prothrombinase and tenase (factor IXa, factor VIIIa and factor x) catalytic complexes on the membrane surface of intact activated platelets and platelet-derived microparticles, following thrombin-mediated activation of the non-enzymatic cofactors V and VIII, respectively. Tans, G. et al., *Blood*, 77:2641 (1991). This positive feedback process results in the local generation of large concentrations of thrombin within the vicinity of the thrombus which supports further thrombus growth and extension. Mann, K. G. et al., *Blood*, 76:1 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and proteolytically activate circulating protein C to give activated protein C (aPC). Musci, G. et al., *Biochemistry*, 27:769, (1988). aPC is a serine protease which selectively inactivates the non-enzymatic co-factors Va and VIIIa resulting in a down-regulation of thrombin formation by the prothrombinase and tenase catalytic complexes, respectively. Esmon, C. T., *Science*, 235:1348 (1987). The activation of protein C by thrombin in the absence of thrombomodulin is poor.

Thrombin has also been shown to be a potent direct mitogen for a number of cell types, including cells of mesenchymal, origin such as vascular smooth muscle cells. Chen, L. B. and Buchanan, J. M., *Proc. Natl. Acad. Sci. USA*, 72:131 (1975). The direct interaction of thrombin with vascular smooth muscle also results in vasoconstriction. Walz, D. A. et al., *Proc. Soc. Expl. Biol. Med.*, 180:518 (1985). Thrombin acts as a direct secretagogue inducing the release of a number of bioactive substances from vascular endothelial cells including tissue plasminogen activator. Levin, E. G. et al., *Thromb. Haemost.*, 56:115 (1986). In addition to these direct effects on vascular cells, the enzyme can indirectly elaborate potent mitogenic activity on vascular smooth muscle cells by the release of several potent growth factors (e.g., platelet-derived growth factor and epidermal growth factor) from platelet a-granules following thrombin-induced activation. Ross, R., *N. Engl. J. Med.*, 314:408 (1986).

Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively. Ross, A. M., *Thrombosis in Cardiovascular Disorder*, p. 327, W. B. Saunders Co. (Fuster, V. and Verstraete, M. edit. 1991); Califf, R. M. and Willerson, J. T., id. at p 389. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered i.v., has not been shown to be universally effective in the treatment or prevention of acute arterial thrombosis or rethrombosis. Prins, M. H. and Hirsh, J., *J. Am. Coll. Cardiol.*, 67:3A (1991).

Besides the unpredictable, recurrent thrombotic reocclusion which commonly occurs following PTCA, a profound restenosis of the recanalized vessel occurs in 30 to 40% of patients 1 to 6 months following this procedure. Califf, R. M. et al., *J. Am. Coll. Cardiol.*, 17:2B (1991). These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

The need for safe and effective therapeutic anticoagulants has in one aspect focused on the role of the serine protease thrombin in blood coagulation.

Most preferred natural substrates for thrombin are reported to contain an uncharged amino acid in the P3 recognition subsite. For example, the thrombin cleavage site on the Aa chain of fibrinogen, which is the primary physiological substrate for thrombin, is reported to contain a glycine residue in this position while the cleavage site on the Bb chain contains a serine, as shown below:

P4 P3 P2 P1 P1'

Gly-Gly-Val-Arg/Gly Fibrinogen Aa Chain
 [SEQ. ID. NO. 1]
Phe-Ser-Ala-Arg/Gly Fibrinogen Bb Chain
 [SEQ. ID. NO. 2]

Peptidyl derivatives having an uncharged residue in the P3 position are said to bind to the active site of thrombin and thereby inhibit the conversion of fibrinogen to fibrin and cellular activation have been reported. These derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolyl-boroarginine (Ac-(D-Phe)-Pro-boroArg) have been reported to inhibit thrombin by directly binding to the active site of the enzyme. Bajusz, S., *Symposia Biologica Hungarica*, 25:277 (1984); Bajusz, S. et al., *J. Med. Chem*. 33:1729 (1990); Bajusz, S. et al., *Int. J. Peptide Protein Res*. 12:217 (1970); Kettner, C.

and Shaw, E., *Methods Enzymol.*, 80:826 (1987); Kettner, C. et al., EP 293,881 (published Dec. 7, 1988); Kettner, C., et al., *J. Biol. Chem.*, 265:18209 (1990). These molecules have been reported to be potent anticoagulants in the prevention of platelet-rich arterial thrombosis. Kelly, A. B. et al., *Thromb. Haemostas.*, 65:736 at abstract 257 (1991). Other peptidyl aldehydes have been proposed or reported as inhibitors of thrombin. See, e.g., Bey, P. et al., EP 363,284 (published Apr. 11, 1990) and Balasubramanian, N. et al., EP 526,877 (published Feb. 10, 1993).

Peptidyl compounds which are said to be active site inhibitors of thrombin but which differ in structure from those containing an uncharged amino acid in the P3 recognition subsite have been reported.

The compound, Argatroban (also called 2R, 4R-4-methyl-1-[N-2-(3-methyl-1,2,3,4-tetrahydro-8-quinolinesul fonyl)-L-argininyl]-2-piperdinecarboxylic acid), is also reported to bind directly to the active site of thrombin and has been thought to be the most potent and selective compound in the class of non-peptidyl inhibitors of this enzyme. Okamoto, S. et al., *Biochem. Biophys. Res. Commun.*, 101:440 (1981). Argatroban has been reported to be a potent antithrombotic agent in several experimental models of acute arterial thrombosis. Jang, I. K. et al., in both *Circulation*, 81:219 (1990) and *Circ. Res.*, 67:1552 (1990).

Peptidyl compounds which are said to be inhibitors of thrombin and whose mode of action is thought to be by binding to both the active site and another site on the enzyme have been reported. Hirudin and certain peptidyl derivatives of hirudin have been reported to inhibit both conversion of fibrinogen to fibrin and platelet activation by binding to either both the active site and exo site, or the exo site only, of thrombin. Markwardt, F., *Thromb. Haemostas.*, 66:141 (1991). Hirudin is reported to be a 65 amino acid polypeptide originally isolated from leech salivary gland extracts. It is said to be one of the most potent inhibitors of thrombin known. Marki, W. E. and Wallis, R. B., *Thromb. Haemostas.*, 64:344 (1990). It has been reported to inhibit thrombin by binding to both its anion-binding exo-site and to its catalytic active site which are distinct and physically distant from each other. Rydel, T. J. et al., *Science*, 249:277 (1990). Hirudin has been reported to be a potent antithrombotic agent in vivo. Markwardt, F. et al., *Pharmazie*, 43:202 (1988); Kelly, A. B. et al., *Blood*, 77:(1991). In addition to its antithrombotic effects, hirudin has been reported to also effectively inhibit smooth muscle proliferation and the associated restenosis following mechanical damage to an atherosclerotic rabbit femoral artery. Sarembock, I. J. et al., *Circulation*, 84:232 (1991).

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., *J. Biol. Chem.*, 264:8692 (1989); Naski, M. C. et al., *J. Biol. Chem.*, 265:13484 (1990). The region of hirudin represented by hirugen has been reported, as according to by x-ray crystallographic analysis, to bind directly to the exo site of thrombin. Skrzypczak-Jankun, E. et al., *Thromb. Haemostas.*, 65:830 at abstract 507 (1991). Moreover, the binding of hirugen has also been reported to enhance the catalytic turnover of certain small synthetic substrates by thrombin, indicating that a conformational change in the enzyme active site may accompany occupancy of the exo-site. Liu, U. W. et al., *J. Biol. Chem.*, 266:16977 (1991). Hirugen also is reported to block thrombin-mediated platelet aggregation. Jakubowski, J. A. and Maraganore, J. M., *Blood*, 75:399 (1990).

A group of synthetic chimeric molecules comprised of a hirugen-like sequence linked by a glycine-spacer region to the peptide, D-phenylalanyl-prolyl-arginine, which is based on a preferred substrate recognition site for thrombin, has been termed to be hirulog. Maraganore et al., U.S. Pat. No. 5,196,404 (Mar. 23, 1993). The hirugen-like sequence is said to be linked to this peptide through the C-terminal end of the peptide. Maraganone, J. M. et al., *Biochemistry*, 29:7095 (1990). The hirulogs have been reported to be an effective antithrombotic agents in preventing both fibrin-rich and platelet-rich thrombosis. Maraganone, J. M. et al., *Thromb. Haemostas.*, 65:651 at abstract 17 (1991).

Certain benzamidines have been reported to inhibit thrombin though non-selectively. 4-amidinophenylpyruvic acid (APPA) has been reported to be a thrombin inhibitor with low toxicity and favourable pharmacokinetics. However, this compound was reported to be non-selective, inhibiting trypsin, plasmin and kallikrein. Markwardt et al., *Thromb. Res.*, 1:243–52 (1972). Other benzamidine-derived structures which have been reported to inhibit thrombin include the cyclic amides of $N^\alpha$-substituted 4-amidinophenylalanine and 2-amino-5-(4-amidinophenyl)-1-valeric acid. The inhibitory constant displayed by these compounds was reported to be in the micromolar range. Markwardt et al., *Thromb. Res.*, 17:425–31 (1980). Moreover, derivatives of 4-amidinophenylalanine whose α-amino group is linked to the arylsulfonyl residue via a ω-aminoalkylcarboxylic acid as spacer have also been assessed for their inhibitory effect. Among these $N^\alpha$-(2-naphthylsulphonylglycyl)-4-amidino-phenylalanine piperi-dide (a-NAPAP) has been reported to possess an affinity for thrombin ($K_i=6\times10^{-9}$ M). Banner et al., *J. Biol. Chem.*, 266:20085 (1991) and Sturzebecher et al., *Thromb. Res.*, 29:635–42 (1983).

Certain bis-benzamidines have been reported to inhibit thrombin. The antithrombin activity of bis-benzamidines was reported to increase with the length and bulkiness of the central chain. However, these compounds were reported to be generally toxic in the micromolar range where they are also inhibitory. Geratz et al., *Thromb. Diath. Haemorrh.*, 29:154–67 (1973); Geratz et al., *J. Med. Chem.*, 16:970–5 (1973); Geratz et al., *J. Med. Chem.*, 19:634–9 (1976); Walsmann et al., *Acta Biol. Med. Germ.*, 35:K1–8 (1976); and Hauptmann et al., *Acta Biol. Med. Germ.*, 35:635–44 (1976).

Certain amidino-bearing aromatic ring structures such as β-naphthamidines have been reported to possess modest antithrombin and anticoagulant activity. This class of compounds include the non-selective 6-amidino-2-naphthyl-4-guanidinobenzoate dimethanesulfonate (FUT 175). Fuji et al., *Biochim. Biophys. Acta*, 661:342–5 (1981); and Hitomi et al., *Haemostasis*, 15:164–8 (1985).

Certain phenylguanidines have been reported to inhibit thrombin. Derivatives of 4-guanidinophenylalanine with inhibitory constants in the micromolar range have been reported to inhibit thrombin. This class includes the $N^\alpha$-tosylated and dansylated 4-guanidino phenylalanine piperidides. Claeson et al., *Thromb. Haemostas.*, 50:53 (1983). Another compound, [ethyl p-(6-guanidinohexanoyloxy) benzoate] methane sulfonate (FOY) was reported to be a non-selective competitive inhibitor of thrombin. Ohno et al., *Thromb. Res.*, 19:579–588 (1980).

Certain compounds having inhibitory activity toward serine proteases, including thrombin, factor Xa, and trypsin, are disclosed within the following commonly assigned United States patents or published PCT applications: U.S. Pat. Nos. 5,371,072; 5,492,895; 5,534,498; 5,597,804; 5,637,599; 5,646,165; 5,656,600; 5,656,645; WO 94/13693; WO 95/35311; WO 95/35313; WO 96/19493.

Substances which interfere in the process of blood coagulation (anticoagulants) have been demonstrated to be important therapeutic agents in the treatment and prevention of thrombotic disorders (Kessler, C. M. (1991) Chest 99: 97S–112S and Cairns, J. A., Hirsh, J., Lewis, H. D., Resnekov, L., and Theroux, P. (1992) Chest 102: 456S–481S). The currently approved clinical anticoagulants have been associated with a number of adverse effects owing to the relatively non-specific nature of their effect on the blood coagulation cascade (Levine, M. N., Hirsh, J., Landefeld, S., and Raskob, G. (1992) Chest 102: 352S–363S). This has stimulated the search for more effective anticoagulant agents which can more effectively control the activity of the coagulation cascade by selectively interfering with specific reactions in this process which may have a positive effect in reducing the complications of anticoagulant therapy (Weitz, J., and Hirsh, J. (1993) J. Lab. Clin. Med. 122:364–373). In another aspect, this search has focused on normal human proteins which serve as endogenous anticoagulants in controlling the activity of the blood coagulation cascade. In addition, various hematophageous organisms have been investigated because of their ability to effectively anticoagulate the blood meal during and following feeding on their hosts suggesting that they have evolved effective anticoagulant strategies which may be useful as therapeutic agents.

SUMMARY OF THE INVENTION

The present invention is directed to novel compounds having a pyridinone or a pyrazinone group at P3 and an optionally substituted heteroaryl group at P1. These compounds have activity as inhibitors of thrombin.

Thus, according to one aspect, the present invention is directed to compounds of formula (I):

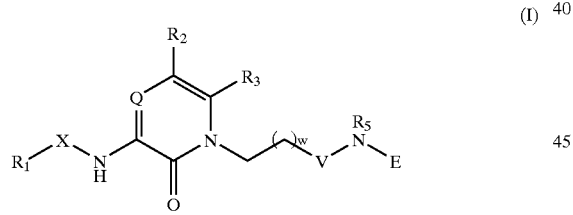

(I)

(a) X is selected from the group consisting of —S(O)$_2$—, —N(R')—S(O)$_2$—, —S(O)$_2$—N(R')—, —C(=O)—, —OC(=O)—, —NHC(=O)—, —C(=O)N(R')—, —P(O)(R')— and a direct link, wherein R' is independently hydrogen, alkyl of 1 to about 4 carbon atoms, aryl of about 6 to about 14 carbon atoms, aralkyl of about 7 to about 16 carbon atoms, with the proviso that when X is —P(O)(R')—, then R' is not hydrogen;

(b) R$_1$ is selected from the group consisting of:
(1) alkyl of 1 to about 12 carbon atoms which is optionally substituted with Y$_1$ and/or Y$_2$,
(2) alkyl of 1 to about 6 carbon atoms substituted with cycloalkyl of about 3 to about 8 carbon atoms which is optionally mono-, di-, or tri-substituted with Y$_1$, Y$_2$ and/or Y$_3$,
(3) cycloalkyl of 3 to about 15 carbon atoms, which is optionally mono-, di-, or tri-substituted on the ring with Y$_1$, Y$_2$ and/or Y$_3$, (4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with Y$_1$, Y$_2$ and/or Y$_3$, (5) heterocyclo of 4 to about 10 ring atoms with the ring atoms selected from carbon and heteroatoms, wherein the heteroatoms are selected from the group consisting of oxygen, nitrogen, and S(O)$_i$, including

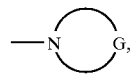

wherein

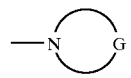

is a 5 to 7 member heterocycle of 3 to 6 ring carbon atoms, where G is —CH$_2$—, —O—, —S(=O)—, —S(O)$_2$— or —S—, which is optionally mono-, di-, or tri-substituted on the ring carbons with Y$_1$, Y$_2$ and/or Y$_3$, (6) alkenyl of 2 to about 6 carbon atoms which is optionally substituted with cycloalkyl of 3 to about 8 carbon atoms, which is optionally mono-, di-, or tri-substituted on the ring carbons with Y$_1$, Y$_2$ and/or Y$_3$, (7) aryl of about 6 to about 14 carbon atoms which is optionally mono-, di- or tri-substituted with Y$_1$, Y$_2$, and/or Y$_3$, (8) heteroaryl of about 5 to about 14 ring atoms with the ring atoms selected from carbon and heteroatoms, wherein the heteroatoms are selected from oxygen, nitrogen, and sulfur, and which is optionally mono-, di-, or tri-substituted with Y$_1$, Y$_2$, and/or Y$_3$, (9) aralkyl of about 7 to about 15 carbon atoms which is optionally substituted on the alkyl chain with hydroxy or halogen and which is optionally mono-, di-, or tri-substituted in the aryl ring with Y$_1$, Y$_2$, and/or Y$_3$,

(10) heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and which is optionally mono-, di- or tri-substituted on the ring with Y$_1$, Y$_2$, and/or Y$_3$,

(11) aralkenyl of about 8 to about 16 carbon atoms which is optionally mono-, di-, or tri-substituted on the aryl ring with Y$_1$, Y$_2$, and/or Y$_3$,

(12) heteroaralkenyl of 5 to 14 ring atoms with the ring atoms selected from carbon and heteroatoms, wherein the heteroatoms are selected from oxygen, nitrogen, and sulfur, and which is optionally mono-, di- or tri-substituted on the ring with Y$_1$, Y$_2$, and/or Y$_3$, (13)

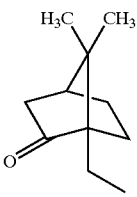

(14)

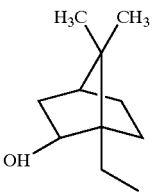

(15)

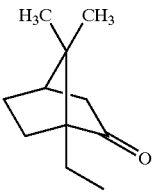

(15)

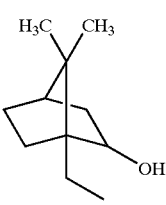

(17) fused carbocyclic alkyl of about 5 to about 15 carbon atoms,
(18) difluoromethyl or perfluoroalkyl of 1 to about 12 carbon atoms,
(19) perfluoroaryl of about 6 to about 14 carbon atoms,
(20) perfluoraralkyl of about 7 to about 15 carbon atoms, and
(21) hydrogen when X is a direct link; wherein
  (i) each $Y_1$, $Y_2$, and $Y_3$ is independently selected from the group consisting of halogen, cyano, nitro, tetrazolyl optionally substituted with alkyl of 1 to about 6 carbon atoms, guanidino, amidino, methylamino, methylguanidino, —$CF_3$, —$CF_2CF_3$, —$CH(CF_3)_2$, —$C(OH)(CF_3)_2$, —$OCF_3$, —$OCF_2CF_3$, —$OCF_2H$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_pZ_1$, —$Z_1$, —$OZ_1$, —$OH$, —$NH_2$, —$NHZ_1$, —$NZ_1Z_2$, N-morpholino, and —$S(O)_p(CF_2)_qCF_3$, wherein p is 0, 1 or 2, q is an integer from 0 to 5, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 5 to about 14 ring atoms, or
  (ii) $Y_1$ and $Y_2$ are selected together to be —$O[C(Z_3)(Z_4)]_rO$— or —$O[C(Z_3)(Z_4)]_{r+1}$—, wherein r is an integer from 1 to 4 and $Z_3$ and $Z_4$ are independently selected from the group consisting of hydrogen, alkyl or 1 to about 12 carbon atoms, aryl of about 6 to about 14 carbon atoms, heteroaryl of about 5 to about 14 ring a atoms having 1 to about 9 carbon atoms, aralkyl of about 7 to about 15 carbon atoms, and heteroaralkyl of about 5 to about 14 ring atoms;

(c) Q is —N— or —$C(R_4)$—;
(d) $R_2$ is selected from the group consisting of hydrogen, halogen and alkyl of 1 to about 6 carbon atoms;
(e) $R_3$ is selected from the group consisting of hydrogen, alkyl of 1 to about 6 carbon atoms, cycloalkyl of 3 to about 7 carbon atoms, alkoxy of 1 to about 6 carbon atoms, halogen, and trifluoromethyl;
(f) alternatively, $R_2$ and $R_3$ are selected together and are —$(CH_2)_k$— where k is 3 or 4;
(g) $R_4$ is selected from the group consisting of hydrogen, alkyl of 1 to about 8 carbon atoms, hydroxy, alkoxy of 1 to about 8 carbon atoms, aralkyl of 7 to about 15 carbon atoms, alkyl of 1 to about 5 carbon atoms substituted with cycloalkyl of 3 to about 8 carbon atoms, —$NHR_8$, —$S(O)_tR_8$ and —$C(=O)R_8$ where t is 0, 1 or 2;
(h) w is 0, 1 or 2;
(i) V is —$CH(R_9)$—, —$C(=O)$—, —O—, —$S(O)_2$— or a direct link;
(j) $R_5$ is hydrogen or alkyl of 1 to about 6 carbon atoms;
(k) E is heteroaryl of about 6 to about 10 ring atoms having from 1 to about 4 ring nitrogen atoms and the remainder of the ring atoms carbon atoms and which is substituted with $R_6$ and $R_7$;
(l) $R_6$ and $R_7$ are independently selected from the group consisting of hydrogen, halogen, hydroxy, alkyl of 1 to about 6 carbon atoms, alkoxy of 1 to about 6 carbon atoms, alkyl of 1 to about 4 carbon atoms substituted with alkoxy of 1 to about 4 carbon atoms, trifluoromethyl, —$C(=O)OR_{10}$, —$NHR_{10}$, —$C(=O)R_{10}$, —$C(=O)NHR_{10}$, —$OC(=O)NHR_{10}$, —$C(=NR_{10})NHR_{11}$, and —$N(R_{12})$—$C(=NR_{10})NHR_{11}$; and
(m) $R_8$, $R_9$, $R_{10}$, $R_{11}$ and $R_{12}$ are independently selected from the group consisting of hydrogen, alkyl of 1 to about 6 carbon atoms and —$(CF_2)_jCF_3$ wherein j is 0, 1, 2 or 3; and pharmaceutically acceptable salts thereof.

In one aspect, the present invention is directed to compounds which are potent inhibitors of thrombin. According to a preferred aspect, these compounds comprise novel serine protease inhibitors. The present invention is also directed to pharmaceutical compositions which comprise one of these compounds and a pharmaceutically acceptable carrier. These compounds and pharmaceutical compositions are potent inhibitors of blood coagulation in vitro and in vivo in mammals. These compounds and pharmaceutical compositions may be used as therapeutic agents for treating disease states in mammals which are characterized by abnormal thrombosis. A further aspect of the present invention is directed to the use of these compounds and pharmaceutical compositions for treatment of disease states in mammals characterized by abnormal thrombosis. An alternate aspect of the present invention is directed to methods of using these thrombin inhibitors as in vitro diagnostic agents.

In yet another aspect, the present invention is directed to methods of using the compounds and pharmaceutical compositions of the present invention for the prevention of thrombosis in a mammal suspected of having a condition characterized by abnormal thrombosis, comprising administering to said mammal a therapeutically effective amount of a compound of the present invention or pharmaceutical composition comprising such a compound.

In referring to formula (I), P1, P2, P3 and P4 denote the portions of the molecule indicated in formula (Ia) below:

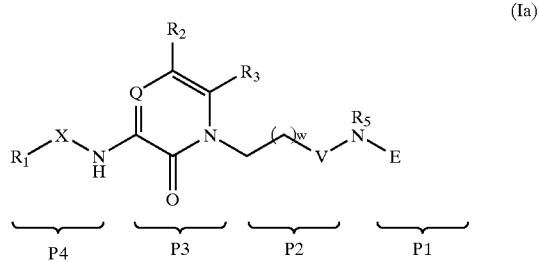

(Ia)

wherein $R_1$, $R_2$, $R_3$, $R_5$, $R_6$, X, Q and V are as defined in connection with formula (I).

Definitions

In accordance with the present invention and as used herein, the following terms are defined to have following meanings, unless explicitly stated otherwise:

The term "acyl" refers to the group —C(=O)R' wherein R' is a hydrocarbyl group.

The term "alkenyl" refers to unsaturated aliphatic groups having at least one double bond.

The term "alkynyl" refers to unsaturated aliphatic groups having at least one triple bond.

The term "alkyl" refers to saturated aliphatic groups including straight-chain, branched-chain and cyclic groups.

The terms "alkoxy" and "alkoxyl" refer to a group having the formula, R—O—, wherein R is an alkyl group.

The term "alkoxycarbonyl" refers to —C(O)OR wherein R is alkyl.

The term "aminoalkyl" refers to an alkyl group substituted with an amino ($NH_2$) group.

The term "aralkenyl" refers to an alkenyl group substituted with an aryl group. Preferably the alkenyl group has from 2 to about 6 carbon atoms.

The term "aralkyl" refers to an alkyl group substituted with an aryl group. Suitable aralkyl groups include benzyl, picolyl, and the like, all of which may be optionally substituted. Preferably the alkyl group has from 1 to about 5 carbon atoms.

The term "aryl" refers to an aromatic group which has at least one ring having a conjugated pi electron system and includes a carbocyclic aryl, heterocyclic aryl and biaryl groups, all of which may be optionally substituted.

The term "aryloxy" refers to a group having the formula, R—O—, wherein R is an aryl group.

The term "aralkoxy" refers to a group having the formula, R—O—, wherein R is an aralkyl group.

The term "amino acid" refers to both natural and unnatural amino acids in their D and L stereoisomers, if their structures allow such stereoisomeric forms, and their analogs. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, demosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid residue" refers to radicals having the structure: (1) —C(O)—R—NH—, wherein R typically is —CH(R')—, wherein R' is H or a carbon containing substituent; or (2)

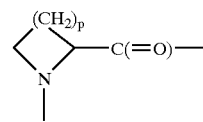

wherein p is 1, 2 or 3 representing the azetidinecarboxylic acid, proline or pipecolic acid residues, respectively.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycerine; or alanine carboxamide is an amino acid analog of alanine.

"Arginine mimic side chain" or "side chain of an arginine mimic" refers to a group of atoms which spatially and electronically resemble or mimic the normal arginine side chain. These groups include the cyclic $R_5$ groups defined in connection with formula (I).

"Biaryl" refers to phenyl substituted by carbocyclic or heterocyclic aryl as defined herein, ortho, meta or para to the point of attachment of the phenyl ring.

"Brine" refers to an aqueous saturated solution of sodium chloride.

"Camphor derivative" refers to the groups:

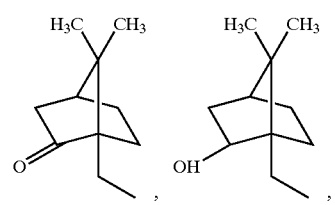

-continued

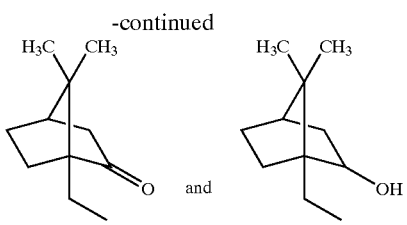

and

"Carbocyclic" refers to a group having one or more rings wherein the ring atoms are all carbon atoms and includes groups having aryl, cycloalkyl, and unsaturated cycloalkyl or a combination of such rings. Such groups include cyclohexyl, cycloheptenyl, tetrahydronaphthyl, phenyl, naphthyl, and the like.

"Carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocyclic aryl groups include phenyl and naphthyl. Suitable substituted carbocyclic aryl groups include indene and phenyl substituted by one to two substituents such being advantageously lower alkyl, hydroxy, lower alkoxy, lower alkoxycarbonyl, halogen, trifluoromethyl, nitro, and cyano. Substituted naphthyl refers to 1- or 2-naphthyl substituted by lower alkyl, lower alkoxy, or halogen.

"Carboxylate mimic" or "carboxylic acid mimic" refers to a group which spatially and electronically mimics a carboxylic acid and provides a net negative charge, i.e., an anion, and also has a pKa value similar to that of a corresponding carboxylic acid, preferably having a pKa of about 4 to 5.

"Cycloalkenyl" or "unsaturated cycloalkyl" refers to a cyclic alkenyl group, that is, a cycloalkyl group modified by having at least one double band. Suitable cycloalkenyl groups include, for example, cyclopentenyl and cyclohexenyl.

"Cycloalkyl" refers to a cyclic alkyl group. Suitable cycloalkyl groups include, for example, cyclohexyl, cyclopropyl, cyclopentyl, and cycloheptyl.

"Cyclohexylmethyl" refers to a cyclohexyl group attached to $CH_2$.

"Fused carbocyclic" refers to a group having multiple rings which are fused, including multicyclic fused carbocyclic rings having both aromatic and non-aromatic rings. Suitable fused carbocyclic rings include fluorenyl, tetralin and the like.

"Fused carbocyclic alkyl" refers to an alkyl group substituted with a fused carbocyclic ring moiety, preferably a multicyclic fused carbocyclic ring having both aromatic and nonaromatic rings. Suitable fused carbocyclic alkyl groups include fluorenyl methyl and the like.

The term "halogen" refers to fluorine, chlorine, bromine and iodine.

"A heteroatom" as defined herein is an atom other than carbon or hydrogen, e.g., typically, oxygen, nitrogen or sulfur.

"Heterocyclic" refers to a group having 1 or more rings wherein the ring atoms are carbon atoms or heteroatoms, and includes rings that are reduced, saturated, unsaturated and aromatic and, if the group has more than one ring, includes a combination of such rings. Suitable heteroatoms include oxygen, nitrogen and $S(O)_i$ wherein i is 0, 1 or 2. Thus, heterocyclic groups include groups having (i) heterocyclo rings (ii) unsaturated heterocyclo rings, (iii) heteroaryl rings or (iv) a combination of such rings.

"Heteroaryl" refers to aromatic groups having a mixture of carbon atoms and heteroatoms. Preferred heteroaryl groups include those having 5 to 14 ring atoms and from 1 to 9 carbon atoms and the remainder of the ring atoms heteroatoms. Heteroaryl groups include those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroatoms include oxygen, nitrogen, and sulfur. Typical heteroaryl groups include furanyl, thienyl, pyridyl, pyrrolyl, pyrimidyl, pyrazinyl, imidazolyl, pyrazolyl, oxazolyl, thiazolyl and the like.

"Heteroaralkenyl" refers to an alkenyl group substituted with a heteroaryl group. Preferably the alkenyl group has from 2 to about 6 carbon atoms.

"Heteroaralkyl" refers to an alkyl group substituted with a heteroaryl group. Preferably the alkyl group has from 1 to about 6 carbon atoms.

A "heteroatom" as defined herein is an atom other than carbon or hydrogen, e.g., typically oxygen, nitrogen or sulfur.

"Heterocyclo" refers to a reduced heterocyclic ring system comprised of carbon, nitrogen, oxygen and/or sulfur atoms, and includes such heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Unsaturated heterocyclo" refers to a heterocyclo group which is modified by having at least one double bond, but which is not aromatic.

"Heterocycloalkyl" refers to an alkyl group substituted with a heterocyclo group. Preferably the alkyl group has from 1 to about 6 carbon atoms.

The term "hydrocarbyl" denotes an organic radical composed of carbon and hydrogen which may be aliphatic (including alkyl, alkenyl and alkynyl groups and groups which have a mixture of saturated and unsaturated bonds), alicyclic (such as cycloalkyl), aromatic (such as aryl) or combinations thereof, and may refer to straight-chained, branched-chain or to cyclic structures or to radicals having a combination thereof, as well as to radicals substituted with halogen atom(s) or heteroatoms, such as nitrogen, oxygen and sulfur and their functional groups (such as amino, alkoxy, aryloxy, lactone groups, and the like), which are commonly found in organic compounds and radicals.

The term "hydroxyalkyl" refers to an alkyl group substituted with a hydroxy group.

The term "lower" referred to herein in connection with organic radicals or compounds defines such with up to and including 6, preferably up to and including 4 and advantageously one or two carbon atoms. Such groups may be straight chain or branched chain.

"Perfluoroalkyl" refers to an alkyl group which has every hydrogen replaced with fluorine.

"Perfluoroaryl" refers to an aryl group which has every hydrogen replaced with fluorine.

"Perfluoroarylalkyl" or "Perfluoroaralkyl" refers an aralkyl group in which every hydrogen on the aralkyl moiety is replaced with fluorine.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

The term "quaternary ammonium salt" refers to compounds produced by reaction between a basic nitrogen in an R substituent and an alkylhalide, arylhalide, and aralkylhalide. Other reactants with good leaving groups may also be used, such as alkyl trifluoromethanesulfonates, alkyl methanesulfonates, and alkyl p-toluenesulfonates. A quaternary ammonium salt has a positively charged nitrogen in the R substituent. Pharmaceutically acceptable counterions include Cl—, Br$^{31}$, I⁻, CF$_3$C(O)O⁻ and CH$_3$C(O)O⁻. The counterion of choice can be made using ion exchange resin columns. R groups with basic nitrogens include —CH$_2$CH$_2$CH$_2$NHC(=NH)NH$_2$, —CH$_2$

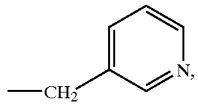

—(CH$_2$)$_p$NH$_2$, wherein p is an integer from 1 to 6. For example, the following R groups contain basic nitrogens: 3-(R)-quinuclidine, 3-(S)-quinuclidine, 3-yl-2-ethyl-4(3H)-quinazolinone, ethyl morpholine, ethyl piperidine, 2-(2-ethyl)pyridine, and 4-(methyl)-5-hydroxy-6-methyl-3-pyridine methanol.

"Trihydrocarbylsilyl" refers to the group

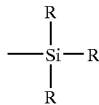

wherein each R is an independently selected hydrocarbyl group.

The term "terminal carbon" refers to the carbon atom of a straight chain alkyl which is furthest from the parent structure.

In addition, the following abbreviations stand for the following:

The symbol "=" when adjacent to a variable in text represents a double bond, e.g., (=x).

"AcN" or "MeCN" refers to acetonitrile
"Ac$_2$O" refers to acetic anhydride.
"AIBN" refers to 2,2'-azobisisobutyronitrile.
"9-BBN" refers to 9-borabicyclo[3.3.1]nonane.
"Bn" refers to benzyl.
"Boc" or "BOC" refers to t-butoxycarbonyl.
"Boc$_2$O" refers to Boc anhydride (di-tert-butyl dicarbonate).
"BOP" refers to benzotriazol-1-yl-oxy-tris-(dimethylamino)-phosphonium hexafluorophosphate.
"BnSO$_2$" or "BzlSO$_2$" refers to benzylsulfonyl.
"t-BuOK" refers to potassium tert-butoxide.
"Cbz" or "CBz" refers to benzyloxycarbonyl.
"CsOAc" refers to Cesium acetate.
W "DCA" refers to dichloroacetic acid.
"DCC" refers to N,N'-dicyclohexylcarbodiimide.
"DCE" refers to 1,2-dichloroethane.
"DCM" refers to dichloromethane (also called methylene chloride).
"DEAD" refers to diethyl azodicarboxylate.
"DHP" refers to 3,4-dihydro-2H-pyran.
"DIEA" refers to diisopropylethylamine.
"DMF" refers to N,N-dimethylformamide.
"DMSO" refers to dimethyl sulfoxide.
"DMAP" refers to 4-dimethylaminopyridine.
"DPPA" refers to diphenylphosphoryl azide.

"EDAC" or "EDC" refers to 1-ethyl-3-(3-dimethylaminopropyl) carbodiimide hydrochloride salt.
"Et$_3$N" refers to triethylamine.
"EtOAc" or "EA" refers to ethyl acetate.
"EtOH" refers to ethanol.
"HATU" refers to O-(7-azabenzotriazol-1-yl)-1,1,3,3-tetramethyluronium hexafluorophosphate.
"HBTU" refers to 2-(1H-benzotriazol-1-yl)-1,1,3,3-tetramethyluronium hexafluorophosphate.
"HCl" refers to hydrochloric acid.
"Hex" refers to hexane.
"HOAc" refers to acetic acid.
"HOAt" refers to 1-hydroxy-7-azabenzotriazole.
"HOBt" refers to 1-hydroxybenzotriazole monohydrate.
"HPLC" refers to high pressure liquid chromatography.
"i-BuOCOCl" refers to isobutyl chloroformate.
"KOAc" refers to potassium acetate.
"LiAlR$_4$" refers to lithium aluminum hydride.
"LiAlH$_2$(OEt)$_2$" refers to lithium diethoxy aluminum hydride.
"Me" refers to methyl.
"MeOH" refers to methanol.
"NaOH" refers to sodium hydroxide.
"NBS" refers to N-bromosuccinimide.
"NMM" refers to N-methylmorpholine.
"Ph$_3$P" or "PPh$_3$" refers to triphenylphosphine.
"2-PrPen" refers to 2-propylpentanoyl.
"pTSA" refers to para-toluenesulfonic acid.
"TBTU" refers to 2-(1H-benzotriazol-1-yl)-1,1,3,3-tetramethyluronium tetrafluoroborate.
"TEA" refers to triethylamine.
"TFA" refers to trifluoroacetic acid.
"THF" refers to tetrahydrofuran.
"TLC" refers to thin layer chromatography.

BRIEF DESCRIPTION OF THE DRAWINGS

Figure 1A:
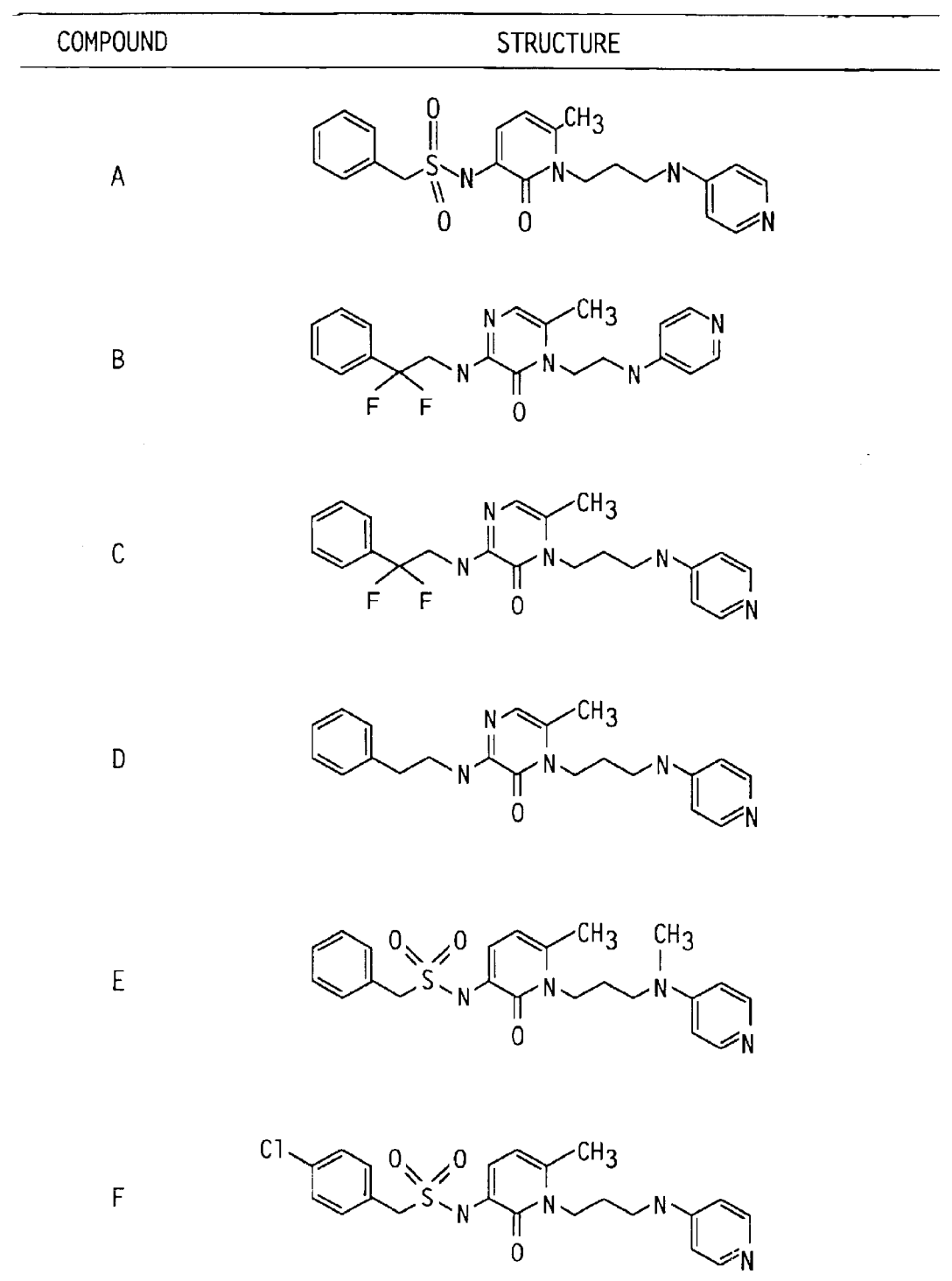
Figure 1B:
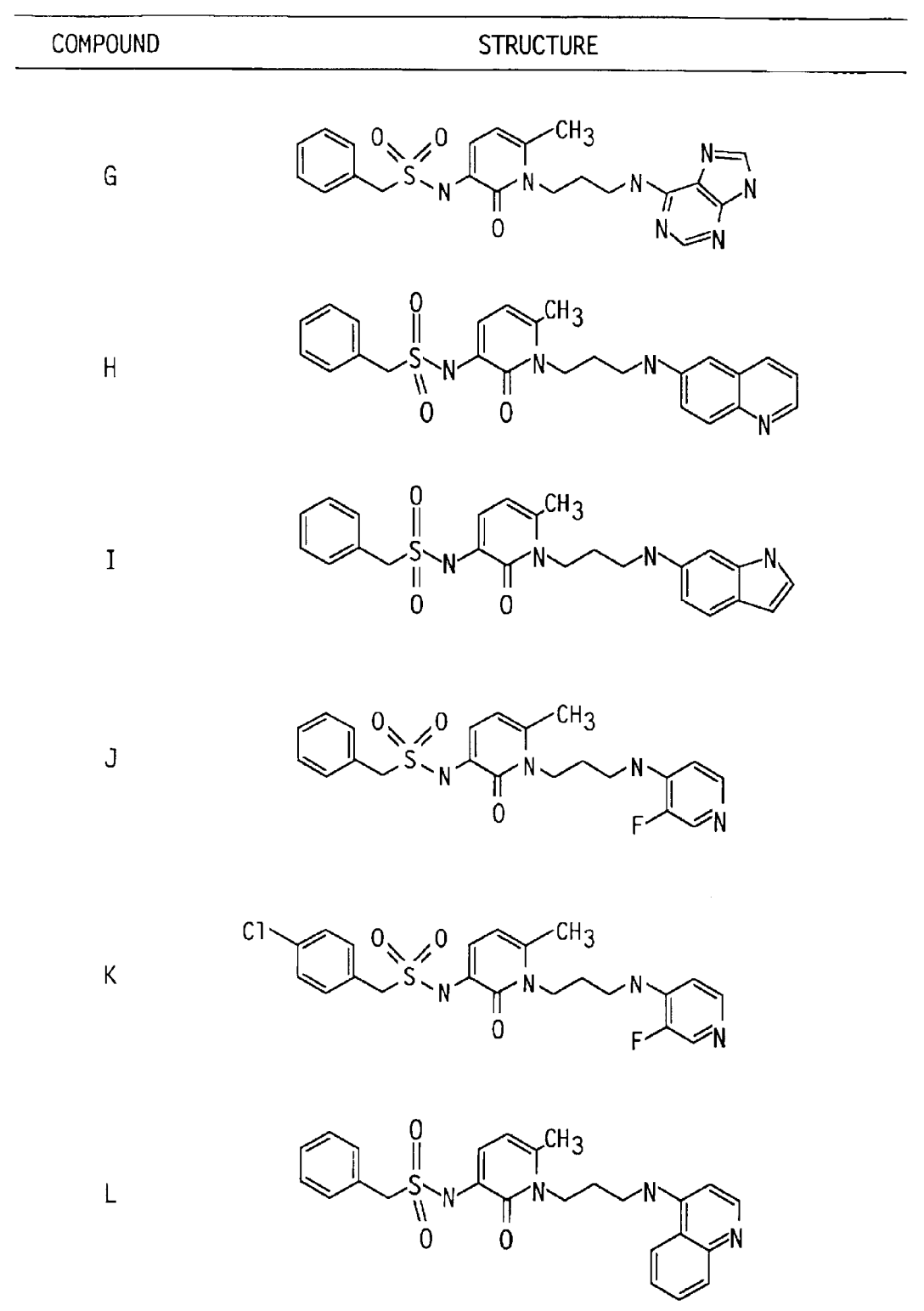

FIGS. 1A, 1B and 1C depict certain preferred compounds of the present invention.

DETAILED DESCRIPTION OF THE INVENTION

1. Preferred Compounds

Figure 1C:
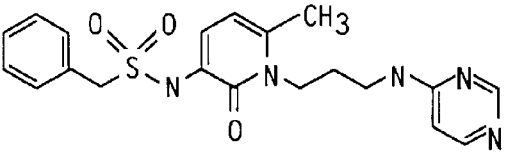
Figure 1C:
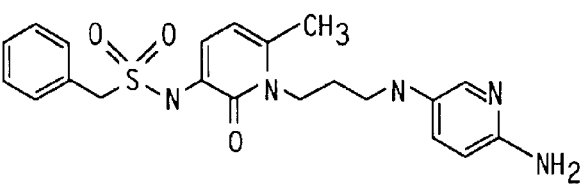
Figure 1C:
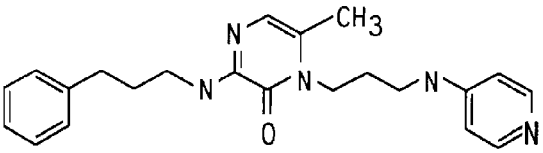
Figure 1C:
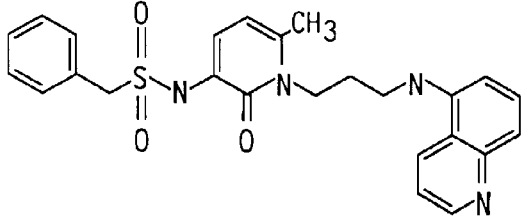
Figure 1C:
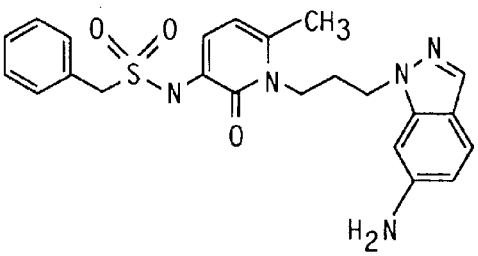
Figure 1C:
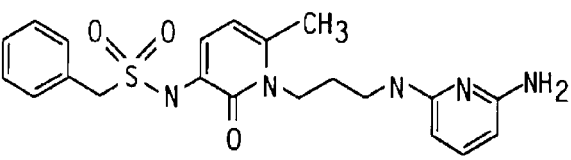

A preferred aspect of the present invention is directed to compounds of formula (I):

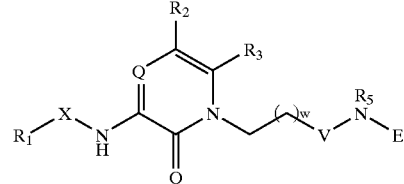

(a) X is selected from the group consisting of —S(O)$_2$—, —N(R')—S(O)$_2$—, —S(O)$_2$—N(R')—, —C(=O)—, —OC(=O)—, —NHC(=O)—, —C(=O)N(R')—, —P(O)(R')— and a direct link, wherein R' is independently hydrogen, alkyl of 1 to about 4 carbon atoms, aryl of about 6 to about 14 carbon atoms, aralkyl of about 7 to about 16 carbon atoms, with the proviso that when X is —P(O)(R')—, then R' is not hydrogen;

(b) R$_1$ is selected from the group consisting of:
(1) alkyl of 1 to about 12 carbon atoms which is optionally substituted with Y$_1$ and/or Y$_2$,
(2) alkyl of 1 to about 6 carbon atoms substituted with cycloalkyl of about 3 to about 8 carbon atoms which is optionally mono-, di-, or tri-substituted with $Y_1$, $Y_2$ and/or $Y_3$,
(3) cycloalkyl of 3 to about 15 carbon atoms, which is optionally mono-, di-, or tri-substituted on the ring with $Y_1$, $Y_2$ and/or $Y_3$,
(4) heterocycloalkyl of 4 to about 10 ring atoms with the ring atoms selected from carbon and heteroatoms, wherein the heteroatoms are selected from the group consisting of oxygen, nitrogen, and $S(O)_i$, wherein i is 0, 1 or 2, which is optionally mono-, di-, or tri-substituted on the ring with $Y_1$, $Y_2$ and/or $Y_3$,
(5) heterocyclo of 4 to about 10 ring atoms with the ring atoms selected from carbon and heteroatoms, wherein the heteroatoms are selected from the group consisting of oxygen, nitrogen, and $S(O)_i$, including

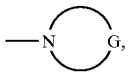

wherein

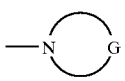

is a 5 to 7 member heterocycle of 3 to 6 ring carbon atoms, where G is —$CH_2$—, —O—, —S(=O)—, —$S(O)_2$— or —S—, which is optionally mono-, di-, or tri-substituted on the ring carbons with $Y_1$, $Y_2$ and/or $Y_3$,
(6) alkenyl of 2 to about 6 carbon atoms which is optionally substituted with cycloalkyl of 3 to about 8 carbon atoms, which is optionally mono-, di-, or tri-substituted on the ring carbons with $Y_1$, $Y_2$ and/or $Y_3$,
(7) aryl of about 6 to about 14 carbon atoms which is optionally mono-, di- or tri-substituted with $Y_1$, $Y_2$, and/or $Y_3$,
(8) heteroaryl of about 5 to about 14 ring atoms with the ring atoms selected from carbon and heteroatoms, wherein the heteroatoms are selected from oxygen, nitrogen, and sulfur, and which is optionally mono-, di-, or tri-substituted with $Y_1$, $Y_2$, and/or $Y_3$,
(9) aralkyl of about 7 to about 15 carbon atoms which is optionally substituted on the alkyl chain with hydroxy or halogen and which is optionally mono-, di-, or tri-substituted in the aryl ring with $Y_1$, $Y_2$, and/or $Y_3$,
(10) heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and which is optionally mono-, di- or tri-substituted on the ring with $Y_1$, $Y_2$, and/or $Y_3$,
(11) aralkenyl of about 8 to about 16 carbon atoms which is optionally mono-, di-, or tri-substituted on the aryl ring with $Y_1$, $Y_2$, and/or $Y_3$,
(12) heteroaralkenyl of 5 to 14 ring atoms with the ring atoms selected from carbon and heteroatoms, wherein the heteroatoms are selected from oxygen, nitrogen, and sulfur, and which is optionally mono-, di- or tri-substituted on the ring with $Y_1$, $Y_2$, and/or $Y_3$,

(13) 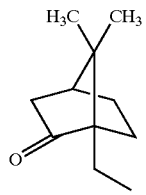

(14) 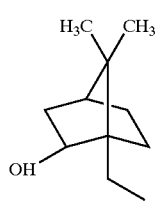

(15) 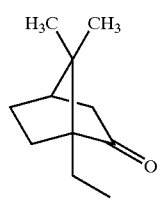

(15) 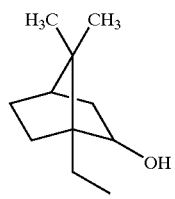

(17) fused carbocyclic alkyl of about 5 to about 15 carbon atoms,
(18) difluoromethyl or perfluoroalkyl of 1 to about 12 carbon atoms,
(19) perfluoroaryl of about 6 to about 14 carbon atoms,
(20) perfluoraralkyl of about 7 to about 15 carbon atoms, and
(21) hydrogen when X is a direct link; wherein
(i) each $Y_1$, $Y_2$, and $Y_3$ is independently selected from the group consisting of halogen, cyano, nitro, tetrazolyl optionally substituted with alkyl of 1 to about 6 carbon atoms, guanidino, amidino, methylamino, methylguanidino, —$CF_3$, —$CF_2CF_3$, —$CH(CF_3)_2$, —$C(OH)(CF_3)_2$, —$OCF_3$, —$OCF_2CF_3$, —$OCF_2H$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NZ_1Z_2$, —$C(O)OH$, —$C(O)$ $OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_pZ_1$, —$Z_1$, —$OZ_1$, —$OH$, —$NH_2$, —$NHZ_1$, —$NZ_1Z_2$, N-morpholino, and —$S(O)_p(CF_2)_qCF_3$, wherein p is 0, 1 or 2, q is an integer from 0 to 5, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 5 to about 14 ring atoms, or (ii) $Y_1$ and $Y_2$ are selected together to be —O[C($Z_3$)($Z_4$)]$_r$O— or —O[C($Z_3$)($Z_4$)]$_{r+1}$, wherein r is an integer from 1 to 4 and $Z_3$ and $Z_4$ are independently selected from the group consisting of hydrogen, alkyl or 1 to about 12 carbon atoms, aryl of about 6 to about 14 carbon atoms, heteroaryl of about 5 to about 14 ring atoms having 1 to about 9 carbon atoms, aralkyl of about 7 to about 15 carbon atoms, and heteroaralkyl of about 5 to about 14 ring atoms;

(c) Q is —N— or —C($R_4$)—;

(d) $R_2$ is selected from the group consisting of hydrogen, halogen and alkyl of 1 to about 6 carbon atoms;

(e) $R_3$ is selected from the group consisting of hydrogen, alkyl of 1 to about 6 carbon atoms, cycloalkyl of 3 to about 7 carbon atoms, alkoxy of 1 to about 6 carbon atoms, halogen, and trifluoromethyl;

(f) alternatively, $R_2$ and $R_3$ are selected together and are —(CH$_2$)$_k$— where k is 3 or 4;

(g) $R_4$ is selected from the group consisting of hydrogen, alkyl of 1 to about 8 carbon atoms, hydroxy, alkoxy of 1 to about 8 carbon atoms, aralkyl of 7 to about 15 carbon atoms, alkyl of 1 to about 5 carbon atoms substituted with cycloalkyl of 3 to about 8 carbon atoms, —NHR$_8$, —S(O)$_t$R$_8$ and —C(=O)R$_8$ where t is 0, 1 or 2;

(h) w is 0, 1 or 2;

(i) V is —CH($R_9$)—, —C(=O)—, —O—, —S(O)$_2$— or a direct link;

(j) $R_5$ is hydrogen or alkyl of 1 to about 6 carbon atoms;

(k) E is heteroaryl of about 6 to about 10 ring atoms having from 1 to about 4 ring nitrogen atoms and the remainder of the ring atoms carbon atoms and which is substituted with $R_6$ and $R_7$;

(l) $R_6$ and $R_7$ are independently selected from the group consisting of hydrogen, halogen, hydroxy, alkyl of 1 to about 6 carbon atoms, alkoxy of 1 to about 6 carbon atoms, alkyl of 1 to about 4 carbon atoms substituted with alkoxy of 1 to about 4 carbon atoms, trifluoromethyl, —C(=O)OR$_{10}$, —NHR$_{10}$, —C(=O)R$_{10}$, —C(=O)NHR$_{10}$, —OC(=O)NHR$_{10}$, —C(=NR$_{10}$)NHR$_{11}$, and —N(R$_{12}$) —C(=NR$_{10}$)NHR$_{11}$; and (m) $R_8$, $R_9$, $R_{10}$, $R_{11}$ and $R_{12}$ are independently selected from the group consisting of hydrogen, alkyl of 1 to about 6 carbon atoms and —(CF$_2$)$_j$CF$_3$ wherein j is 0, 1, 2 or 3; and pharmaceutically acceptable salts thereof.

Preferred X groups include —S(O)$_2$—, and a direct link. Especially preferred, according to one aspect, for X is —S(O)$_2$—. According to an alternate aspect, especially preferred for X is a direct link.

Preferred $R_1$ groups include alkyl, substituted aralkyl, aryl, substituted aryl, alkyl substituted with $Y_1$ and/or $Y_2$ and alkyl substituted with optionally substituted cycloalkyl. According to one aspect of the present invention, particularly preferred $R_1$ substituents include substituted or unsubstituted phenylethyl, substituted or unsubstituted benzyl and alkyl substituted with cycloalkyl wherein the cycloalkyl is substituted with an aryl or heteroaryl group. According to one especially preferred aspect, $R_1$ is 4-chlorobenzyl, phenylethyl, pyridylethyl, 1-phenyl-cyclopropyl, 2-(1-phenyl-cyclopropyl)-ethyl, 2-(1-pyridyl-cyclopropyl)-ethyl, or phenyl-(2,2-difluoro)ethyl. According to an alternate preferred aspect, $R_1$ is alkyl substitued with $Y_1$ and/or $Y_2$ wherein $Y_1$ and $Y_2$ are independently phenyl or substituted phenyl or alkyl substituted with cycloalkyl which is optionally substituted on the ring with $Y_1$ wherein $Y_1$ is phenyl or substituted phenyl.

Preferred $P_3$ groups include those where Q is —N— or —C($R_4$)— where $R_4$ is hydrogen. According to one preferred aspect, Q is —N—. According to an alternate preferred aspect, Q is —C($R_4$)— where $R_4$ is hydrogen. Particularly preferred are $P_3$ groups where $R_2$ is hydrogen, especially preferred $P_3$ groups include those wherein $R_3$ is methyl.

Preferred V groups include —CH($R_9$)—. Preferred $R_9$ groups include hydrogen and methyl.

Suitable heteroaryl groups for E include mono- and bi-cyclic heteroaryl groups which are substituted with $R_6$ and $R_7$.

Preferred heteroaryl groups for E include

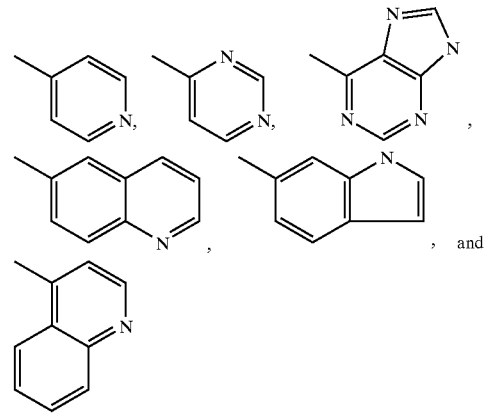

, and all substituted with $R_6$ and $R_7$.

According to one preferred aspect, E is

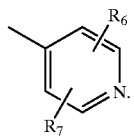

Preferred $R_6$ and $R_7$ groups include hydrogen, halogen, lower alkyl, lower alkoxy and amino.

According to a preferred aspect, especially preferred are compounds where X is —S(O)$_2$— or a direct link, $R_1$ is substituted or unsubstituted benzyl or substituted or unsubstituted phenylethyl, Q is —N— or —C($R_4$)— where $R_4$ is hydrogen, $R_2$ is hydrogen, $R_3$ is methyl, V is —CH($R_9$)— where $R_9$ is hydrogen and $R_6$ and $R_7$ are hydrogen.

Preferred compounds include Compounds A to R depicted in FIGS. 1A and 1B.

2. General Information Regarding Synthesis

Certain compounds used in the synthesis of the compounds of the present invention may be purchased from commercially available sources such as Sigma, Fluka, Aldrich, Nova and Calbiochem or synthesized by one skilled in the art. See, e.g., Owens, T. D.; Semple, J. E. *Bioorg. Med. Chem. Lett.* 1998, 8, 3683. Semple, J. E.; Rowley, D. C.; Owens, T. D.; Minami, N. K.; Uong, T. H.; Brunck, T. K. ibid. 1998, 8, 3525. Semple, J. E. *Tetrahedron Lett.* 1998, 39, 6645. Semple, J. E. *Bioorg. Med. Chem. Lett.* 1998, 8, 2501. Reiner, J. R.; Lim-Wilby, M. S.; Brunck, T. K.; Uong, T. H.;

Goldman, E. A.; Abelman, M. A., Nutt, R. F.; Semple, J. E.; Tamura, S. Y. *Bioorg. Med. Chem. Lett.* 1999, 9, 895. Abelman, M. M.; Miller, T. A.; Nutt, R. F. U.S. Pat. No. 5,696,231, 1997. Marlowe, C. K.; Scarborough, R. M.; Laibelman, A. M.; Sinha, U.; Zhu. B.-Y. U.S. Pat. No. 5,721,214, 1998.

$R_1X$ may be purchased from commercially available sources such as Sigma, Fluka, Aldrich, Nova and Calbiochem or synthesized by one skilled in the art. See, e.g., Sanderson, P. E. J., et al., *J. Med. Chem.* 1998, 41, 4466–4474; Miller, W. D.; Tao, E. V. P. U.S. Pat. No. 5,387,681 (1995).

Preferred means of chemically coupling (as for example, amide bond function) include formation of a peptide bond by using conventional coupling reagents known in the art. See Bodanszky, N., *Peptide Chemistry*, pp. 55–73, Springer-Verlag, New York (1988) and references cited therein. The chemical coupling may be either by means of one-step or two-step coupling. In one-step coupling, the two coupling partners are coupled directly. Preferred coupling reagents for one-step coupling of the coupling partners include DCC with HOBt, EDC with HOBt, HBTU or TBTU. In two-step coupling, an activated ester or anhydride of the C-terminal carboxy group of one coupling partner is formed prior to its coupling to the other coupling partner.

For preparation of certain compounds having hydrogenation sensitive substituent groups, it is preferred to avoid the use of hydrogen gas with palladium on carbon for hydrogenation steps. Another preferred method for preparing compounds of the present invention containing hydrogenation sensitive groups such as alkenyl or aryl moieties substituted with halogen, cyano, nitro, or $—S—Z_1$, is to use boron tris(trifluoroacetate), $B(OCOCF_3)3$, to cleave protecting groups such as the $N^g$-nitro of an arginine side chain. The reagent is prepared by the reaction of $BBr_3$ and $CF_3COOH$ in dichloromethane at 0° C. The reagent is also commercially available. Generally, the $N^g$-nitro compound is treated with boron tris(trifluoroacetate) in trifluoroacetic acid at 0° C. See, e.g., Fieser, M. and Fieser, L. F., Reagents for Organic Synthesis, p. 46, John Wiley & Sons, New York (1974); Pless, J., and Bauer, W. *Angew. Chem., Internat. Ed.*, 12, 147 (1973).

In addition, another preferred reagent for selective nitro group cleavage is titanium trichloride. This reagent is commercially available. The $N^g$ nitro compound is treated with titanium trichloride in aqueous methanol containing an ammonium acetate buffer followed by exposure of the reaction mixture to air or dimethyl sulfoxide. Freidinger, R. M., Hirschmann, R., and Veber, D. F., *J. Org. Chem.*, 43, 4800 (1978).

3. Selection of Preferred Compounds

According to one aspect of the present invention, preferred compounds of the present invention are selected for their potency and selectivity toward inhibition of serine proteases, especially thrombin. Such evaluations are routinely performed in vitro, following procedures such as those set forth in Example A. As described therein, and as generally known, a target serine protease and its substrate are combined under assay conditions permitting reaction of the protease with its substrate. The assay is performed in the absence of test compound and, also, in the presence of increasing concentrations of the test compound. The concentration of test compound at which 50% of the serine protease activity is inhibited by the test compound is the $IC_{50}$ value (Inhibitory Concentration) or $EC_{50}$ (Effective Concentration) value for that compound. Within a series or group of test compounds, those having lower $IC_{50}$ or $EC_{50}$ values are considered more potent inhibitors of the serine protease than those compounds having higher $IC_{50}$ or $EC_{50}$ values. The $IC_{50}$ measurement is often used for more simplistic assays, whereas the $EC_{50}$ is often used for more complicated assays, such as those employing cells. $K_i$ is calculated from the $IC_{50}$.

Preferred compounds according to this aspect of the present invention have a $K_i$ value of 100 nM or less as measured in an in vitro assay for inhibition of thrombin activity. Especially preferred compounds have a $K_i$ value of less than 30 nM.

The test compounds also are evaluated for selectivity toward a serine protease. As described in the Examples, and as generally known, a test compound is assayed for its potency toward a panel of serine proteases and other enzymes and an $IC_{50}$ value or $EC_{50}$ value is determined for each test compound in each assay system. A compound that demonstrates a low $IC_{50}$ value or $EC_{50}$ value or corresponding low $K_i$ value for the target enzyme, e.g., thrombin, and a higher $IC_{50}$ value or $EC_{50}$ value for other enzymes within the test panel, is considered to be selective toward the target enzyme. Generally, a compound is deemed selective if its $IC_{50}$ value or $EC_{50}$ value (or $K_i$ value) in the target enzyme assay is at least one order of magnitude less than the next smallest $IC_{50}$ value or $EC_{50}$ value measured in the selectivity panel of enzymes.

The compounds of the present invention are screened for their ability to inhibit some or all of thrombin, factor Xa, plasmin, recombinant tissue plasminogen activator (rt-PA), activated protein C (aPC), chymotrypsin, and trypsin. Certain of the preferred compounds are distinguished by their ability to inhibit thrombin, while not substantially inhibiting some or all of factor Xa, plasmin, tissue plasminogen activator (t-PA), activated protein C (aPC), chymotrypsin, and/or trypsin. With respect to thrombin and the other enzymes and as used herein, the term "not substantially inhibiting" means that the $IC_{50}$ (or $K_i$) for factor Xa, plasmin, t-PA, aPC, chymotrypsin, and/or trypsin for a given compound is greater than or equal to its $IC_{50}$ (or $K_i$) for thrombin. Preferably the ratio of $IC_{50}$'s for factor Xa, trypsin, and the other enzymes, to $K_i$ ($IC_{50}$) for thrombin will be at least about 25 or greater, more preferably about 100 or greater. It is believed that the ability to selectively inhibit thrombin will result in therapeutic benefits to patients.

With respect to compounds within the present invention that inhibit members within the trypsin/chymotrypsin family, including trypsin, chymotrypsin, elastase, and serine proteases involved in the coagulation cascade, "not specifically inhibiting" means the $IC_{50}$ or $K_i$ for the target enzyme is less than or equal to the $IC_{50}$ or $K_i$ for non-target enzymes contacted with the inhibitor.

For screening compounds using these assays, the compounds of the present invention are dissolved in buffer to give solutions containing concentrations such that assay concentrations range from 0 to 100 micromolar. In the assays for thrombin, factor Xa, plasmin, t-PA, aPC, chymotrypsin, and trypsin, a chromogenic synthetic substrate is added to a solution containing test compound and the enzyme of interest and the residual catalytic activity of that enzyme is determined spectrophotometrically. The $IC_{50}$ of a test compound of the present invention is determined from the rate of substrate turnover caused by the specific enzyme being measured. $IC_{50}$ is the concentration of test compound which gives 50% inhibition of the rate of substrate turnover. Likewise, the $K_i$ of a compound of the present invention is determined from the rate of substrate turnover caused by the specific enzyme being measured at various enzyme concentrations. Example A provides exemplars of in vitro assays used to select the compounds of the present invention.

Certain of the preferred compounds of the present invention have a $K_i$ of about 0.001 to about 200 nM in the thrombin assay. Especially preferred compounds have a $K_i$ of about 0.001 to about 50 nM. The more especially preferred compounds have a $K_i$ of about 0.001 to about 10 nM.

Certain of the preferred compounds of the present invention have a $IC_{50}$ for factor Xa, plasmin, t-PA, aPC, chymotrypsin, and/or trypsin which is at least 10 times greater than its $K_i$ for thrombin. Especially preferred compounds have an $IC_{50}$ for factor Xa, plasmin, t-PA, aPC, chymotrypsin, and/or trypsin which is about 20 to about 100,000 times greater than its $K_i$ for thrombin. More especially preferred compounds have an $IC_{50}$ for factor Xa, plasmin, t-PA, aPC, chymotrypsin, and/or trypsin which is about 100 to about 1,000,000 times greater than its $K_i$ for thrombin. In the event that a compound of the present invention has an $IC_{50}$ with respect to factor Xa, plasmin, t-PA, aPC, chymotrypsin, or trypsin which is greater than the highest concentration of compound tested, the highest concentration of compound tested is considered to be the reported $IC_{50}$.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

The therapeutically effective amount of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

Pharmaceutically acceptable carriers for therapeutic use are well known in the pharmaceutical art, and are described, for example, in *Remington's Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixirs for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

5. Utility and Methods

Compounds of the present invention when made and selected as disclosed are useful as potent inhibitors of thrombin in vitro and in vivo. As such, these compounds are useful as in vitro diagnostic reagents to prevent the clotting of blood and as in vivo pharmaceutical agents to prevent, inhibit and/or attenuate thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vacuum therein as a means to draw blood obtained by venipuncture into the tube is well known in the medical arts. Kasten, B. L., "Specimen Collection", *Laboratory Test Handbook*, 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of thrombin, and as such, can be incorporated into blood collection tubes to prevent clotting of the mammalian blood drawn into them.

The compounds of the present invention are used alone, in combination with other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

The compounds of the present invention are useful as a pharmaceutical agent for preventing, inhibiting and/or attenuating thrombosis in a mammal suspected of having a condition characterized by abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The present invention includes methods for preventing a condition in a mammal suspected of having a condition characterized by abnormal thrombosis, comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets capsules or elixirs taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a "therapeutically effective amount" of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts. Typically, administration of the compounds or pharmaceutical composition of the present invention is commenced at lower dosage levels, with dosage levels being increased until the desired effect of preventing in vivo thrombosis is achieved which would define a therapeutically effective amount. For the compounds of the present invention, alone or as part of a pharmaceutical composition, such doses are between about 0.01 mg/kg and 100 mg/kg body weight, preferably between about 0.01 and 10 mg/kg, body weight.

Certain compounds of the present invention have utility as inhibitors of proteases within the trypsin/chymotrypsin class of enzymes. Members of that class include, but are not limited to, elastase, chymotrypsin, and the serine proteases trypsin, thrombin, factor Xa, and factor VIIa. With respect to the inhibitors within the present invention directed at serine proteases acting within the coagulation cascade, e.g., inhibitors of thrombin, factor Xa and factor VIIa, such have in vitro and in vivo utilities as provided hereinabove for thrombin inhibitors.

Elastase has been implicated in a variety of conditions, including pulmonary hypertension (Rabinovitch, M., *Acta Paediatr. Jpn* 37:657–666 (1995)), idiopathic pulmonary fibrosis, rheumatoid arthritis, adult respiratory distress syndrome, cystic fibrosis, and other inflammatory diseases and conditions (Doring, G., Am. *J. Respir. Crit. Care Med.* 150: S114–S117 (1994)). Inhibition of elastase was shown to prevent or retard progression of pulmonary hypertension (Rabinovitch). Thus, inhibitors of the present invention directed toward elastase are useful as pharmaceutical compositions for the inhibition of elastase in conditions where elastase activity is associated with a pathological condition.

Elevated levels of chymotrypsin and trypsin are associated with the pathological effects resulting from pancreatitis (see U.S. Pat. No. 5,534,498). Animal studies of chemically-induced pancreatitis suggest that the disorder is rooted in the inability of pancreatic acinar cells to excrete digestive proenzymes, resulting in activation of trypsinogen to trypsin by lysosomal hydrolases within the cell. The amount of trypsin produced exceeds protective levels of protease inhibitor normally available.

The elevated levels of trypsin then cause activation of the other digestive enzymes co-localized with trypsin in the lysosome, such as chymotrypsin. The net effect of the enzyme activation is pancreatitis, which is characterized by damage to the pancreas and surrounding tissues from auto-digestion of the cells by the various digestive enzymes. These activated digestive enzymes also cause edema, interstitial hemorrhage, vascular damage, coagulation necrosis, fat necrosis and parenchymal cell necrosis.

Inhibitors of the present invention directed toward either trypsin or chymotrypsin, or other members of the trypsin/chymotrypsin family that contribute to the deleterious effects of pancreatitis, are useful for the prevention and treatment of pancreatitis in mammals.

In addition to the in vivo utilities, inhibitors of the present invention also find utility in vitro. Inhibitors of enzymes within the coagulation cascade are useful inhibitors of blood coagulation in vitro, as described hereinabove. Inhibitors of other enzymes within the trypsin/chymotrypsin family, including trypsin, chymotrypsin, and elastase, are useful reagents in in vitro assays designed to measure the activity of such enzymes.

For instance, to determine or confirm the presence of active trypsin, chymotrypsin, or elastase in a sample, the activity of the enzyme in the sample is determined in the presence and absence of the specific inhibitor (which may be labeled using a radioactive or other detectable label). Lower activity measured in the presence of inhibitor as compared to in the absence of inhibitor demonstrates inhibition of the enzyme and, thus, its presence in the sample.

Similarly, the level of activity of an enzyme present in a sample is determined by adding inhibitor to the sample in a range of titrating doses, and calculating activity of the enzyme at each escalating dose of inhibitor. The concentration of inhibitor that completely inhibits the enzyme in the assay, along with knowledge of the assay parameters and characteristic of enzyme inhibition, allows one to calculate the activity of the enzyme in the sample.

The level of chymotrypsin measured in stool samples in vitro is used as an indicator of pancreatitis (Riedel, L. et al., *Gut* 32:321–324 (1991); Chari, S., *Trop. Gastroenterol.*, 11:144–147 (1990)). Chymotrypsin inhibitors of the present invention are useful in such assays to evaluate the level of active chymotrypsin in such a sample, according to protocols such as those outlined hereinabove.

An additional use of the inhibitors of the present invention is their use to quench enzymatic reactions effected by the target enzyme. Thus, to control or prevent digestion of a sample with trypsin or chymotrypsin, an inhibitor of trypsin or chymotrypsin, respectively, is added in inhibit the target enzyme and, thus, control or prevent digestion by that enzyme.

Certain compounds of the present invention can also be useful inhibitors of elastase, and are therefore useful pharmaceutical agents for the control of inflammation.

To assist in understanding, the present invention will now be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

Preparation of 3-Benzyloxycarbonylamino-1-[(2-methoxy-carbonyl)ethyl]-6-methyl-2-pyridinone (1-2)

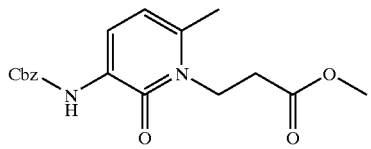

Methyl acrylate (5.23 mL, 58.14 mmol) was added to a solution of 3-benzyloxycarbonylamino-6-methyl-2-pyridinone (1-1) (10.0 g, 38.76 mmol) and cesium carbonate (3.16 g, 9.7 mmol) in 50 mL of dry DMF under nitrogen. The reaction mixture was stirred at room temperature for 15 hours, then was poured into water (500 mL), and then was extracted with ethyl acetate (800 mL). The organic phase was washed with brine (300 mL), dried over sodium sulfate, and concentrated under reduced pressure. The crude residue was purified by silica gel column chromatography using EtOAc and hexane (2:1) as eluant to afford the title compound 1-2 (7.74 g, 58 % yield) as a light yellow solid. MS (m/e): 345 (M+1)$^+$. TLC: $R_f$(0.36)(EA/Hex); $^1$H NMR (400 MHz, DMSO): δ 2.3 (s, 3H), 2.68 (t, 2H), 3.60 (s, 3H), 4.2 (t, 2H), 5.1 (s, 2H), 6.1 (d, 1H), 7.4 (m, 5H), 7.6 (d, 1H), 8.1 (s, 1H)

EXAMPLE 2

Preparation of 3-Amino-1-[(2-methoxycarbonyl)ethyl]-6-methyl-2-pyridinone (1-3)

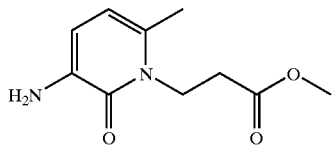

A mixture of 1-2 (7.74 g, 22.5 mmol) and 10% palladium on carbon catalyst (0.93 g) in tetrahydrofuran and methanol was stirred at room temperature under hydrogen at 1 atm for 3.5 hours. The reaction mixture was filtered through Celite and evaporated in vacuo to give the title compound 1-3 (5 g, quantitative yield) as a yellow oil. MS (m/e): 211 (M+1). TLC: $R_f$(0.2)(EA/Hex); $^1$H NMR (400 MHz, DMSO): δ 2.3 (s, 3H), 2.68 (t, 2H), 3.6 (s, 3H), 4.1 (t, 2H), 5.8 . (d, 1H), 6.8 (d, 1H).

EXAMPLE 3

Preparation of 3-(Benzylsulfonylamino)-1-[(2-methoxy-carbonyl)ethyl]-6-methyl-2-pyridinone (1-4)

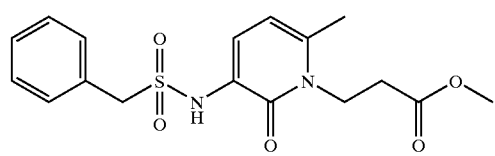

To a solution of 1-3 (5.0 q, 23.81 mmol) in MeCN (60 mL) was added benzylsulfonyl chloride (5.45 g, 28.57 mmol) and 2,6-lutidine (4.16 mL, 35.72 mmol). The resulting mixture was stirred at room temperature for 12 hours. Solvent was removed under reduced pressure. The residue was then diluted with ethyl acetate (500 mL). The organic phase was washed with 0.1N HCl (250 mL) and brine (250 mL). After being dried with sodium sulfate and filtered, the residue was concentrated and purified by silica gel column chromatography using ethyl acetate and hexane (3:1) as eluant solvents to afford the title compound 1-4 (7.8 g, 99% yield) as a yellow solid. MS (m/e): 365 (M+1). TLC: $R_f$ (0.28)(EA/Hex); $^1$H NMR (400 MHz, CD$_3$OD): δ 2.4 (s, 3H), 2.8 (t, 2H), 3.6 (s, 3H), 4.3 (t, 2H), 4.4 (s, 2H), 6.08 (d, 1H), 7.3(m, 6H).

EXAMPLE 4

Preparation of 3-(Benzylsulfonylamino)-6-methyl-1-(3-hydroxypropyl)pyridone (1-5)

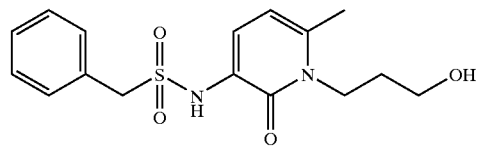

To a solution of compound 1-4 (15.86 g, 43.57 mmol) in THF (150 mL) containing 5% of methanol at −10° C., was added sodium borohydride (6.6 g, 174.29 mmol). After 3.5 hours, water was added and the mixture was partitioned with dichloromethane. The organic phase was dried over sodium sulfate and concentrated under reduced pressure to afford the title compound 1-5 (14.42 g, 99% yield) as a yellow solid. MS (m/e): 337 (M+1). TLC: $R_f$(0.24)(EA); $^1$H NMR (400 MHz, DMSO): δ 1.7 (m, 2H), 2.2 (s, 3H), 3.4 (t, 2H), 4.0 (t, 2H), 4.5 (s, 2H), 6.0 (d, 1H), 7.02(d, 1H), a 7.3(m, 5H).

EXAMPLE 5

Preparation of 3-(Benzylsulfonylamino)-6-methyl-1-(3-bromopropyl)pyridone (1-6)

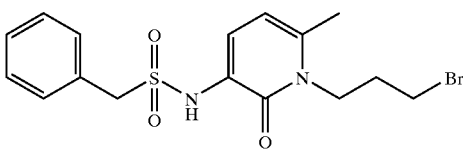

A solution of triphenylphosphine (0.46 g, 1.75 mmol) in DMF (5 mL) was added to a mixture of 1-5 (0.49 g, 1.46 mmol) and carbon tetrabromide (0.68 g, 2.05 mmol) in DMF (5 mL) at 0° C. The resulting mixture was allowed to warm to room temperature and allowed to stir for 12 hours. The mixture was then concentrated under reduced pressure. The crude residue was purified by silica gel column chromatography using ethyl acetate and hexane (3:1 to 2:1 gradient) as eluants to afford the title compound 1-6 (0.38 g, 66% yield) as a yellow solid. MS (m/e): 399. TLC: $R_f$ (0.35) (EA/Hex); 1H NMR (400 MHz, CDCl$_3$): δ 2.23 (m, 2H), 2.4 (s, 3H), 3.5 (t, 2H), 4.2 (t, 2H), 4.3 (s, 2H), 6.0 (d, 1H), 7.2(d, 1H), 7.3(m, 5H).

EXAMPLE 6

Preparation of 3-(Benzylsulfonylamino)-6-methyl-1-[3-(4-aminopyridine)propyl]pyridone (1-7)

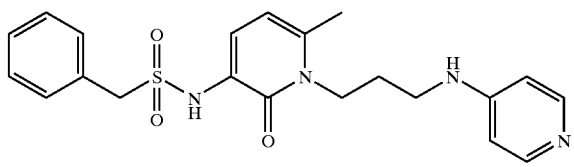

To a solution of 1-6 (0.2 g, 0.50 mmol) in dioxane and DMF (1:1) (5 mL) was added 4-aminopyridine (0.04 g, 0.42 mmol) and 2,6-lutidine (0.074 mL, 0.63 mmol). The resulting mixture was stirred at 90° C. for 16 hours. The solvent was removed under reduced pressure. The crude residue was purified via RP-HPLC using (0 to 35% gradient) MeCN/H$_2$O/(0.1%)TFA as eluant solvents to afford the title compound 1-7 (120 mg, 60% yield) as a white powder. MS (m/e): 413 (M+1). HPLC 8.93 minutes (MeCN % 5–75), 12.43 minutes (MeCN % 10–40). $^1$H NMR (400 MHz, DMSO): δ 2.1 (m, 2H), 2.2 (s, 3H), 4.0 (t, 2H), 4.2 (t, 2H), 4.5 (s, 2H), 6.0 (d, 1H), 6.8(d, 2H), 7.02(d, 1H), 7.3(m, 5H), 8.03(s, 1H), 8.2(d, 2H), 8.5(s, 1H).

EXAMPLE 7

Preparation of Ethyl(ethyl 3-aminopropionate)oxamide (2-2)

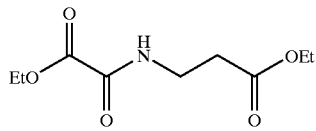

Diethyl oxalate, (17.7 mL, 130.2 mmol), triethylamine (9.1 mL, 65.1 mmol) and beta-alanine ethyl ester hydrochloride (10 g, 65.1 mmol) were dissolved in 30 mL ethanol and heated to 50° C. under a steady stream of nitrogen. After approximately 5 hours, TLC showed the reaction was complete. After concentration in vacuo, the residue was dissolved in 30 mL dichloromethane, and washed with 15 mL water (3×). The organic layers were dried with anhydrous sodium sulfate and concentrated in vacuo. Purification by flash chromatography, eluting with hexane/ethyl acetate (4/1→1/1), yielded the oxamide (13.06 g, 93%), as a colorless liquid; the product was verified by NMR. $^1$H NMR (CDCl$_3$): δ 7.63 (br s, 1H), 4.35 (q, 2H), 4.18 (q, 2H), 3.61 (q, 2H), 2.59 (q, 2H), 1.38 (t, 3H), 1.27 (t, 3H).

EXAMPLE 8

Preparation of (2-Hydroxypropylamino)-(ethyl 3-aminopropionate)oxamide (2-3)

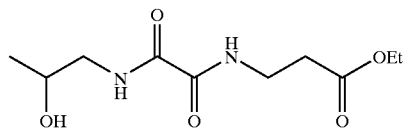

Ethyl(ethyl 3-aminopropionate)oxamide (2-2) (13.06 g, 60.1 mmol) was dissolved in 65 mL of ethanol at room temperature under a steady stream of nitrogen; to this mixture 1-amino-2-propanol (4.64 ml, 60.1 mmol) was added in one portion. After 3 hours, the reaction mixture solidified and TLC showed the reaction to be complete. The residue was dissolved in chloroform, evaporated in vacuo to dryness, and reconcentrated from chloroform to yield 14.1 g (95%) of the title compound as a white solid; the product was verified by NMR. $^1$H NMR (CDCl$_3$): δ 7.9–7.8 (br d, 2H), 4.18 (q, 2H), 4.0 (br s, 1H), 3.61 (q, 2H), 3.5 (m, 1H), 3.2 (q, 1H), 2.58 (t, 2H), 2.3 (br s, 1H), 1.61 (br s, 1H), 1.27 (t, 3H), 1.22 (d, 3H).

EXAMPLE 9

Preparation of (2-Oxopropylamino)-(ethyl 3-aminopropionate)oxamide (2-4)

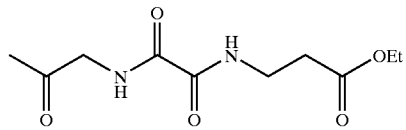

To a stirred slurry at 50° C. under argon of (2-hydroxypropylamino)-(ethyl 3-aminopropionate)

oxamide (2-3) (14.1 g, 57.3 mmol) in 75 mL of water, ruthenium trichloride hydrate (118 mg, 0.573 mmol) was added. When analytical HPLC showed the reaction to be complete, the flask was removed from the heat source and an aqueous solution of sodium bromate (8.65 g, 57.3 mmol) was added dropwise, keeping the reaction temperature below 60° C. The reaction mixture was allowed to come to room temperature and then was diluted with 75 mL ethyl acetate and 30 mL brine. The aqueous layer was extracted with ethyl acetate (3x) and the combined organic layers were washed again with 75 mL brine, dried with anhydrous sodium sulfate and concentrated in vacuo to yield 11.87 g (90%) of the title compound as an off-white solid; the product was verified by NMR. $^1$H NMR (CDCl$_3$): δ 8.0 (br s, 1H), 7.8 (br s, 1H), 4.18 (m, 4H), 3.61 (q, 2H), 2.58 (t, 2H), 2.23 (s, 3H), 1.27 (t, 3H).

EXAMPLE 10

Preparation of 1-[(2-Ethoxycarbonyl)ethyl]-3-hydroxy-6-methylpyrazinone (2-5)

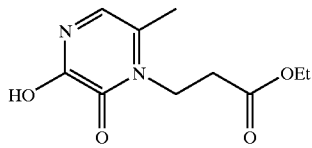

2-5

(2-Oxopropylamino)-(ethyl 3-aminopropionate)oxamide (2-4) (11.87 g, 48.6 mmol) was dissolved in 200 mL acetic acid, trifluroacetic acid (3.7 mL, 48.6 mmol) and trifluoroacetic anhydride (6.8 mL, 48.6 mmol). The reaction mixture was heated to 80° C. under a slow stream of nitrogen for 4 hours. An additional 0.6 equivalents of trifluroacetic acid and trifluoroacetic anhydride were added, and the mixture was allowed to stir overnight. The reaction mixture was concentrated in vacuo. To the residue, 22 mL of acetic acid were added at 60° C. for 15 minutes, then 116 mL of isopropyl acetate was added dropwise. After cooling to room temperature, the mixture was placed in a refrigerator overnight. The next day, the product was suction filtered to give 3.8 g (35%) of a tan solid; the product was verified by NMR. $^1$H NMR (CDCl$_3$): δ 6.15 (s, 1H), 5.3 (s, 1H), 4.16 (m, 4H), 2.76 (t, 2H), 2.19 (s, 3H), 1.25 (t, 3H).

EXAMPLE 11

Preparation of 1-[(2-Ethoxycarbonyl)ethyl]-3-bromo-6-methylpyrazinone (2-6)

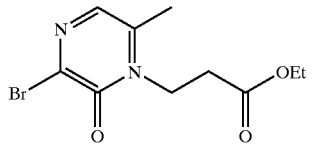

2-6

To a stirred slurry of 1-[(2-ethoxycarbonyl)ethyl]-3-hydroxy-6-methylpyrazinone (2-6) (3.8 g, 16.8 mmol) in 20 mL of dichloromethane, phosphorous oxybromide (5.8 g, 20.2 mmol) was added at 50° C. under a steady stream of N$_2$. The resulting mixture was stirred for 2 hours. The reaction mixture was allowed to cool to room temperature and stirring was continued overnight. The mixture was diluted with 30 mL of chloroform and 30 mL of cold water, basified with ammonium hydroxide, and extracted with 30 mL of chloroform (3x). The combined organic layers were dried over anhydrous sodium sulfate, and concentrated in vacuo to yield the title compound (3.8 g, 80%) as an orange solid; the product was verified by NMR. $^1$H NMR (CDCl$_3$): δ 7.01 (s, 1H), 4.26 (q, 2H), 4.16 (q, 2H), 2.83 (t, 2H), 2.38 (s, 3H), 1.25 (t, 3H).

EXAMPLE 12

Preparation of 2,2-Difluoro-2-phenylacetamide (2-9)

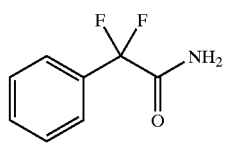

2-9

A mixture of ethylbenzoylformate (2-7) (5g, 28.05 mmol) and (diethylamino)sulfurtrifluoride (2-8) (7.4 mL, 56.11 mmol) was stirred. The temperature rose slowly to 45° C. and then cooled. The reaction mixture was stirred for an additional 2 hours at room temperature and then poured over ice. The oil that formed was taken up in dichloromethane, washed with water, dried over anhydrous magnesium sulfate. The solvent was evaporated to give ethyl-2,2-difluorobenzeneacetate (11 g, 97%) as a pale amber oil. This oil was dissolved in ethanol (80 mL) and saturated with gaseous ammonia for 0.5 hour at ambient temperature. The pressure flask was stoppered and allowed to stand overnight. The solvents were removed to give a yellow solid that was recrystallized from dichloromethane-hexane to give the title compound (8.62 g, 90%) as a tan solid. $^1$H-NMR (methanol-d$_4$): δ 7.41–7.54 (m, 3H), 7.57–7.64(m,2H).

EXAMPLE 13

Preparation of 2,2-Difluoro-2-phenylethylamine (2-10)

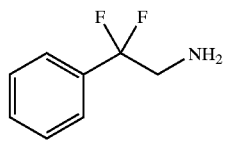

2-10

2,2-Difluoro-2-phenylacetamide (2-9) (7.8 g, 45.03 mmol) was dissolved in THF (200 mL) and cooled to 0° C. with an ice bath. To this stirred solution was added 1M borane-tetrahydrofuran complex (315.2 mL, 315.2 mmol) dropwise over 15 minutes using a dropping funnel. The reaction mixture was aged until the ice bath expired. Upon expiration of the ice bath, the reaction mixture was heated to 70° C. overnight. The reaction mixture was allowed to cool to ambient temperature, then was quenched by the careful dropwise addition of water (100 mL). The mixture was concentrated in vacuo. The residue was diluted with dichloromethane (100 mL) and washed with 10% sodium carbonate. The organic layer was dried over anhydrous sodium sulfate and concentrated in vacuo. The crude residue was purified by flash chromatography (ethyl acetate/hexane) (1:1 to 1:0 gradient) to afford the title compound (6.2 g, 86%) as a yellow oil. ¹H-NMR (CDCl₃): δ 3.15 (t, J=14.0 Hz, 2H), 7.41–7.45 (m, 5H).

EXAMPLE 14

Preparation of 3-(2,2-Difluoro-2-phenylethylamino)-1-[(2-ethoxycarbonyl)ethyl]-6-methylpyrazinone (2-11)

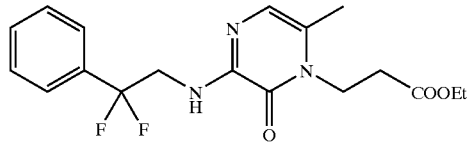

2-11

To a solution of 1-[(2-ethoxycarbonyl)ethyl]-3-bromo-6-methylpyrazinone (2-6) (0.441 g, 1.6 mmol) in toluene (15 mL) was added 2,2-difluoro-2-phenylethylamine (2-10) (0.51 g, 3.2 mmol). The resulting mixture was stirred at 110° C. for 24 hours. The mixture was diluted with ethyl acetate (100 mL) and washed with 10% hydrochloric acid (20 mL) and brine (20 mL). The organic phase was dried over anhydrous sodium sulfate and concentrated under reduced pressure. The crude residue was purified by silica gel column chromatography using ethyl acetate/n-hexane (1:1) as eluent to afford the title compound (0.46 g, 81%) as a pale yellow solid. Rf 0.19 (ethyl acetate/hexane 1/1); ¹H-NMR (CDCl₃): δ 1.26 (t, J=7.2 Hz, 3H), 2.18 (d, J=1.2 Hz, 3H), 2.66 (t, J=6.8 Hz, 2H), 4.06 (dt, J=6.8, 14.4 Hz, 2H), 4.12 (q, J=6.8 Hz, 2H), 4.18 (t, J=7.6 Hz, 2H), 6.11 (t, J=6.4 Hz, 1H), 6.61(d, J=0.8 Hz, 1H), 7.37–7.41 (m, 3H), 7.49–7.53 (m, 2H).

EXAMPLE 15

Preparation of 3-(2,2-Difluoro-2-phenylethylamino)-1-(3-hydroxypropyl)-6-methylpyrazinone (2-12)

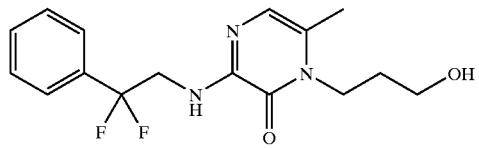

2-12

To a solution of 3-(2,2-difluoro-2-phenylethylamino)-1-[(2-ethoxycarbonyl)ethyl]-6-methylpyrazinone (2-11) (0.37 g, 1.01 mmol) in tetrahydrofuran (10 mL) containing 5% methanol, was added sodium borohydride (0.229 g, 6.07 mmol) at room temperature. The reaction mixture was stirred for 5 hours. Then 2 mL of water was added and the mixture was fractionated between dichloromethane and water. The organic phase was dried over anhydrous sodium sulfate and concentrated under reduced pressure. The crude residue was purified using a silica gel column chromatography with ethyl acetate/n-hexane (1:1) as eluent to afford the title compound (0.305 g, 93%) as a pale yellow solid. Rf 0.28 (MeOH/CH₂Cl₂ 5/95); ¹H-NMR (CDCl₃): δ 1.85 (quintet, J=6.4 Hz, 2H), 2.19 (d, J=1.2 Hz, 3H), 3.47 (q, J=6.4 Hz, 2H), 3.65 (t, J=6.8 Hz, 1H), 4.05 (dt, J=6.4, 14.0 Hz, 2H), 4.12 (t, J=6.4 Hz, 2H), 6.14 (t, J=6.4 Hz, 1H), 6.68(d, J=0.8 Hz, 1H), 7.23–7.41 (m, 3H), 7.49–7.52 (m, 2H).

EXAMPLE 16

Preparation of 3-(2,2-Difluoro-2-phenylethylamino)-1-(3-bromopropyl)-6-methylpyrazinone (2-13)

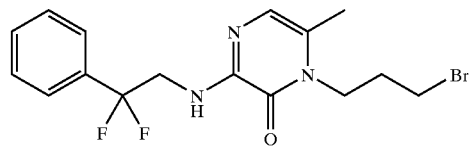

2-13

To a magnetically stirred solution of 3-(2,2-difluoro-2-phenylethylamino)-1-(3-hydroxypropyl)-6-methylpyrazinone (2-12) (0.267 g, 0.82 mmol) and carbon tetrabromide (0.328 g, 0.99 mmol) in dichloromethane (10 mL), was added triphenylphosphine (0.26 g, 0.99 mmol) portionwise with ice-bath cooling. After the addition was complete, the mixture was stirred for an additional 2 hours. The solvent was removed in vacuo. The residue was purified by silica gel column chromatography using ethyl acetate/n-hexane (2:1 to 1:1 gradient) as eluent to afford the title compound (0.309 g, 96.9%) as a yellow solid. Rf 0.45 ((EtOAc/hexane 1/1); ¹H-NMR (CDCl₃): δ 2.20 (d, J=1.2 Hz, 3H), 2.19–2.26 (m, 2H), 3.44 (t, J=6.4 Hz, 2H), 4.01–4.10 (m, 4H 6.12 (t, J=6.4 Hz, 1H), 6.62(d, J=1.2 Hz, 1H), 7.37–7.41 (m, 3H), 7.50–7.53 (m, 2H).

EXAMPLE 17

Preparation of 3-(2,2-Difluoro-2-phenylethylamino)-6-methyl-1-[3-5 (4-aminopyridyl)propyl]-pyrazinone (2-14)

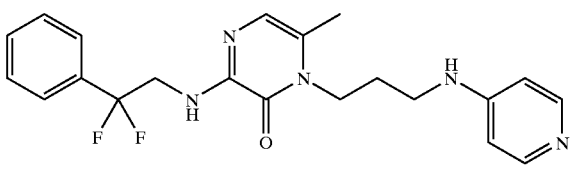

2-14

To a solution of 3-(2,2-difluoro-2-phenylethylamino)-1-(3-bromopropyl)-6-methylpyrazinone (2-13) (0.165 g, 0.42 mmol) in dioxane (15 mL), were added 4-aminopyridine (0.048 g, 0.51 mmol) and 2,6-lutidine (0.099 mL, 0.85 mmol). The resulting mixture was stirred at 90° C. for 15 hours and then concentrated under reduced pressure. The crude residue was purified by RP-HPLC using (0 to 35% gradient) acetonitrile/water/(0.1%) trifluoroacetic acid as eluent to afford the title compound (0.158 g, 92%) as an off-white solid. ¹H-NMR (methanol-d₄): δ 2.21–2.26 (m, 5H), 4.04 (t, J=6.4 Hz, 2H), 4.06 (t, J=14.4 Hz, 2H), 4.22 (t, J=7.6 Hz, 2H), 6.64 (d, J=0.8 Hz, 1H), 6.82 (dd, J=2.4, 6.4 Hz, 2H), 7.44–7.46 (m, 3H), 7.54–7.57 (m, 2H), 8.13 (dd, J=2.0, 5.6 Hz, 2H); MS (m/e) 400.2 (M+1).

EXAMPLE 18

Preparation of 3-Fluoropyridine N-oxide (3-2)

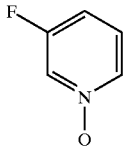

3-2

See Bellas, M. and Suschitzky J., Chem. Soc. 1963, 4007–44009.

A solution of 3-fluoropyridine (3-1) (15 g, 155 mmol), acetic acid (130 mL) and 30% hydrogen peroxide (42 mL) was heated at 80° C. for 24 hours. The solution was concentrated and the residue was dissolved in chloroform and washed with 10% aqueous sodium carbonate. The organic layer was dried with anhydrous sodium sulfate, filtered, and concentrated. The crude product was recrystallized from ethyl acetate and cyclohexanes to give white needles (10.4 g, 58%). $^1$H NMR (400 MHz, CDCl$_3$): 7.07 (m, 1H), 7.26 (m, 1H), 8.08 (m, 1H), 8.18 (m, 1H)

EXAMPLE 19

Preparation of 3-Fluoro-4-nitropyridine N-oxide (3-3)

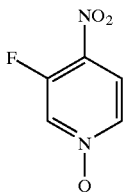

3-3

See Bellas, M. and Suschitzky J., Chem. Soc. 1965, 2096–2100.

To a solution of 3-fluoropyridine N-oxide (3-2) (10.4 g, 90 mmol) in sulfuric acid (52 mL) stirring at 120° C. was added fuming nitric acid (21 mL) over 1 hour. After stirring at 120° C. for another 3 hours, the reaction mixture was cooled to ambient temperature and poured into 300 mL of ice. The pH of the solution was adjusted to pH 7 by addition of 20% sodium hydroxide, and extracted with chloroform. The organic layer was dried, filtered and concentrated. The residue was recrystallized from diethyl ether/hexane to give a pale yellow solid (7.5 g, 51%). $^1$H NMR (400 MHz, CDCl$_3$): 8.05 (m, 2H), 8.22 (m, 1H)

EXAMPLE 20

Preparation of 4-Amino-3-fluoropyridine (3-4)

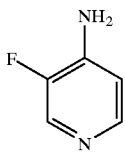

3-4

3-Fluoro-4-nitropyridine N-oxide (3-3) (1.0 g, 6.29 mmol) and FeSO$_4$.H$_2$O (15 g, 37.5 mmol) were suspended in water. Approximately 14 mL of NH$_4$OH was added until a dark color persisted. The resulting mixture was heated to 90° C. for 1 hour under a steady stream of nitrogen. The reaction mixture was allowed to cool to ambient temperature. It was then extracted with 20 mL of diethyl ether (4×), dried with anhydrous sodium sulfate, and concentrated in vacuo to yield the title compound 468 mg (66%) as a brown oil which crystallized upon standing; the product was verified by NMR. $^1$H NMR (CDCl$_3$): δ 8.18 (d, 1H), 8.03 (d, 1H), 6.65 (t, 1H), 4.3 (br, 2H).

EXAMPLE 21

Preparation of 4-Chlorobenzyl sulfonyl chloride (3-6)

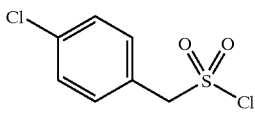

A mixture of thiourea (50 mmol, 3.806 grams) and methanol (25 mL) were heated to near reflux to form a saturated solution. After cooling to ambient temperature, 4-chlorobenzyl chloride (3-5) (8.052 g, 50 mmol) was added and the solution was stirred overnight. Diethyl ether (60 mL) was added to the mixture and crystallization was allowed to finish. The white solid (11.07 g) was collected and dried in vacuo. The white solid was mixed with water (100 mL), and 1,4-dioxane (0 to 50 mL) was added until a clear solution formed. While cooling the solution with an ice bath, chlorine gas was bubbled into the solution for approximately 5 minutes, at which time the solution was saturated. The reaction mixture was purged with nitrogen for 5 minutes. The reaction mixture was diluted with ethyl acetate (400 mL) and washed with water (3×200 mL). The organic layer was dried with sodium sulfate, filtered, and concentrated. The 4-chlorobenzylsulfonyl chloride (7.06 g, 67%) was used without further purification. $^1$H NMR (400 MHz, CDCl$_3$): 4.8 (s, 2H), 7.42 (s, 4H).

EXAMPLE 22

Preparation of 3-(4-Chlorobenzylsulfonylamino)-6-methyl-1-(3-methyl propionate)pyridone (3-7)

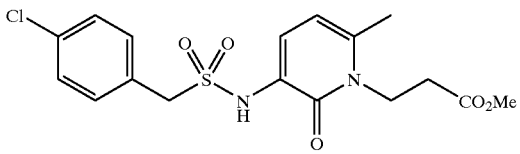

3-7

To a solution of 0.95 g (4.5 mmol) 3-amino-6-methyl-1-(3-methyl propionate)pyridone (1-3) and 1.2 g (5.4 mmol) 4-chlorobenzylsulfonyl chloride (3-6) in acetonitrile under a nitrogen atmosphere, was added 0.78 mL (6.75 mmol) 2,6-lutidine. The reaction mixture was stirred at room temperature for 16 hours. The solvent evaporated in vacuo. The residue was dissolved in ethyl acetate and washed with 0.1 N hydrochloric acid and brine, then dried over anhydrous sodium sulfate, and filtered. The solvent was evaporated in vacuo to afford 1.6 g of the title compound as a viscous oil. $^1$H NMR (400 MHz, CDCl$_3$): δ 2.38 (s, 3H), 2.76 (t, 2H), 3.69 (s, 3H), 4.25 (s, 2H), 4.30 (t, 2H), 5.94 (d, 1H), 7.20–7.26 (m, 5H).

EXAMPLE 23

Preparation of 3-(4-Chlorobenzylsulfonylamino)-6-methyl-1-(3-hydroxypropyl)pyridone (3-8)

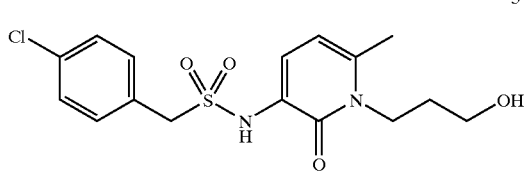

3-8

3-(4-Chlorobenzylsulfonylamino)-6-methyl-1-(3-methyl propionate)pyridone (3-7) (1.6 g, 4.5 mmol) was dissolved in 20 mL tetrahydrofuran and 1 mL methanol and 0.51 g (13.5 mmol) sodium borohydride was added. The reaction mixture was allowed to stir for 16 hours at room temperature and was quenched by addition of 10 mL water. The volatiles were evaporated in vacuo. The residue was partitioned between water and ethyl acetate. The aqueous layer was extracted with ethyl acetate. The combined organic layers were washed with brine, dried over anhydrous sodium sulfate and filtered. The solvent was evaporated in vacuo to afford 1.3 g of the title compound as a white solid. $^1$H NMR (400 MHz, CDCl$_3$): δ 1.90 (m, 2H), 2.38 (s, 3H), 3.51 (t, 2H), 4.26 (s, t, 4H), 6.05 (d, 1H), 7.21–7.33 (m, 5H).

EXAMPLE 24

Preparation of 3-(4-Chlorobenzylsulfonylamino)-6-methyl-1-(3-bromopropyl)pyridone (3-9)

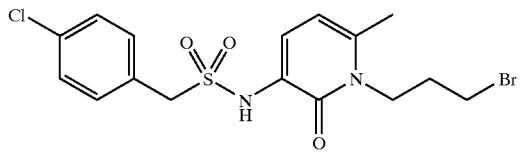

3-9

3-(4-Chlorobenzylsulfonylamino)-6-methyl-1-(3-hydroxypropyl)pyridone (3-8) (292 mg, 0.8 mmol) was dissolved in 8 mL methylene chloride under a nitrogen atmosphere. Triphenylphosphine (250 mg, 0.96 mmol) was added, followed by 370 mg (1.12 mmol) carbon tetrabromide. The reaction mixture was cooled to 0° C. and held at that temperature for 16 hours. The solvent was evaporated in vacuo and the product purified by flash chromatography (50:50 ethyl acetate: hexanes) to afford 227 mg of the title compound as a white solid. $^1$H NMR (400 MHz, CDCl$_3$): δ 2.25 (m, 2H), 2.39 (s, 3H), 3.50 (t, 2H), 4.28 (t, 2H), 4.27 (s, 2H), 5.93 (d, 1H), 7.20–7.31 (m, 5H).

EXAMPLE 25

Preparation of 3-(4-Chlorobenzylsulfonylamino)-6-methyl-1-[3-(4-amino-3-fluoro-pyridine)propyl] pyridone (3-10)

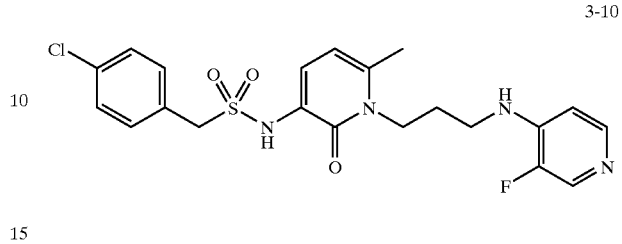

3-10

3-(4-Chlorobenzylsulfonylamino)-6-methyl-1-(3-bromopropyl)pyridone (3-9) (100 mg, 0.251 mmol), 4-amino-3-fluoropyridine (56 mg, 0.502 mmol) (3-4), and 2,6-lutidine (58 μl, 0.502 mmol) were dissolved in 10 mL of dioxane. The mixture was heated for 72 hours at 90° C. with a condensing column under argon. The mixture was concentrated in vacuo, redissolved in 10 mL of acetonitrile/water, and purified via RP-HPLC to yield the title compound 87 mg (81%) as a brown solid; the product was verified by NMR. $^1$H NMR (CD$_3$OD): δ 8.6 (d, 1H), 8.2 (d, 1H), 7.55–7.45 (m, 5H), 7.2 (d, 1H), 7.0 (t, 1H), 6.1 (d, 1H), 4.47 (s, 2H), 4.3 (t, 2H), 4.1 (t, 2H), 2.39 (s, 3H), 2.25 (m, 2H).

EXAMPLE 26

Preparation of Ethyl N-(1-cyanoethyl)-3-aminopropionic acid

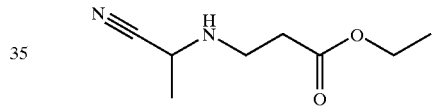

To a suspension of β-alanine ethyl ester hydrochloride (3.23 g, 0.021 mol) in DCM (80 mL) is added Et$_3$N (3.0 mL, 0.021 mol). The resulting mixture is stirred at room temperature for 10 minutes, then acetaldehyde (1.2 mL, 0.021 mol) is added, followed by the drop-wise addition of TMSCN (2.86 mL, 0.021 mol). The resulting mixture is stirred at room temperature for about 18 hours, then is diluted with DCM (100 mL) and is washed with brine (100 mL), dried (Na$_2$SO$_4$), and concentrated in vacuo. The crude mixture is purified by flash column chromatography on silica gel (7:3 EtOAc/hexane). The title compound is isolated as its hydrochloride salt.

EXAMPLE 27

Preparation of 3,5-Dichloro-2-ethoxycarbonylethyl-6-methylpyrazinone

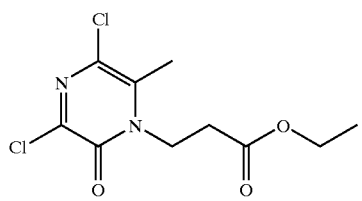

To a suspension of the product of Example 26 (3.06 g, 0.018 mol) in 1,2-dichlorobenzene (20 mL), is added oxalyl chloride (6.34 mL, 0.074 mol). The resulting mixture is stirred at 110° C. for about 18 hours; then the excess oxalyl chloride is quenched by adding coarse silica gel. The resulting mixture is purified 25 by flash column chromatography on silica gel (DCM followed by 1:1 EtOAc/hexane) to afford the title compound.

EXAMPLE 28

Preparation of 5-Chloro-2-ethoxycarbonylethyl-3-hydrazino-6-methylpyrazinone

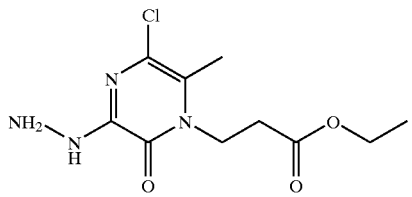

To a solution of the product of Example 26 (10.04 g, 0.036 mol) in dioxane (100 mL), is added hydrazine (3.35 mL, 0.107 mol). The resulting mixture is heated at about 60 to 70° C. After about 2 hours, the reaction mixture is diluted with water (200 mL) and is extracted with EtOAc (3×150 mL). The combined organic phases are washed with brine (300 mL), dried ($Na_2SO_4$), and concentrated under reduced pressure to afford the title compound.

EXAMPLE 29

Preparation of 2-Ethoxycarbonylethyl-3-hydrazino-6-methylpyrazinone

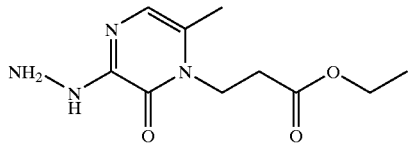

A mixture of the product of Example 27 (7.67 g, 0.028 mol), ammonium formate (7.1 g, 0.112 mol), and Pd/C (10%, 2.0 g) in MeOH (50 mL) is refluxed for 1 hour. The reaction mixture is filtered through Celite and evaporated in vacuo to afford the title compound, which is used in the next step without further isolation.

EXAMPLE 30

Preparation of 3-(2-Benzylsulfonylhydrazino)-6-methyl-1-(3-ethylpropionate)-pyrazinone

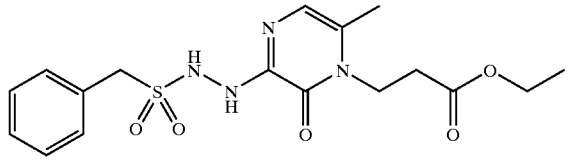

To a mixture of the product of Example 29 (0.096 g, 0.4 mmol) and $Et_3N$ (0.17 mL, 1.2 mmol) in THF (20 mL) is added α-toluenesulfonyl chloride (84 mg, 0.43 mmol). The resulting mixture is stirred at room temperature for 1 hour, then is concentrated in vacuo. The crude residue is diluted with DCM (10 mL), and then TFA (10 mL) is added. The solution is stirred at room temperature for about 1 hour and then is concentrated under reduced pressure. The crude residue is purified by preparative RP-HPLC (water/ACN/TFA) to afford the title compound.

EXAMPLE 31

Preparation of 3-(2-Benzylsulfonylhydrazinyl)-1-(3-hydroxypropyl)-6-methylpyrazinone

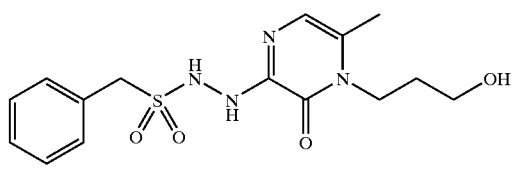

To a solution of 3-(2-benzylsulfonylhydrazino)-1-[(2-ethoxycarbonyl)ethyl]-6-methylpyrazinone, the product of Example 30 (0.398 g, 1.01 mmol), in tetrahydrofuran (10 mL) containing 5% methanol, is added sodium borohydride (0.229 g, 6.07 mmol) at room temperature. The reaction mixture is stirred for 5 hours. Water (2 mL) is then added and the mixture is fractionated between dichloromethane and water. The organic phase is dried over anhydrous sodium sulfate and is concentrated under reduced pressure. The crude residue is purified using silica gel column chromatography with ethyl acetate/n-hexane as eluent to afford the title compound.

EXAMPLE 32

Preparation of 3-(2-Benzylsulfonylhydrazino)-1-(3-bromopropyl)-6-methylpyrazinone

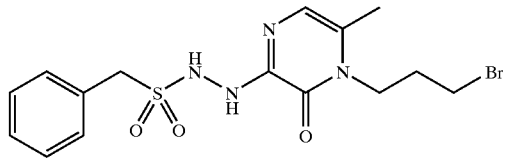

To a magnetically stirred solution of 3-(2-benzylsulfonylhydrazino)-1-(3-hydroxypropyl)-6-methylpyrazinone, the product of Example 31 (0.429 g, 0.82 mmol) and carbon tetrabromide (0.328 g, 0.99 mmol) in dichloromethane (10 mL), is added triphenylphosphine (0.26 g, 0.99 mmol) portionwise with ice-bath cooling. After the addition is complete, the mixture is stirred for about an additional 2 hours. The solvent is removed in vacuo. The residue is purified by silica gel column chromatography using ethyl acetate/n-hexane as eluent to afford the title compound.

EXAMPLE 33

Preparation of 3-(2-Benzylsulfonylhydrazino)-6-methyl-1-[3-(4-aminopyridyl)propyl]-pyrazinone

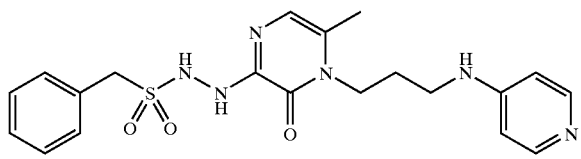

To a solution of 3-(2-benzylsulfonylhydrazino)-1-(3-bromopropyl)-6-methylpyrazinone, the product of Example 32, (0.174 g, 0.42 mmol) in dioxane (15 mL), are added 4-aminopyridine (0.048 g, 0.51 mmol) and 2,6-lutidine (0.099 mL, 0.85 mmol). The resulting mixture is stirred at 90° C. for about 15 hours and then is concentrated under reduced pressure. The crude residue is purified by RP-HPLC using acetonitrile/water/trifluoroacetic acid as eluent to afford the title compound.

EXAMPLE A

In Vitro Enzyme Assays for Specificity Determination

The ability of compounds of the present invention to act as a selective inhibitor of thrombin activity was assessed by determining the concentration of test-compound which inhibited the activity of this enzyme by 50%, ($IC_{50}$) or by determining the $K_i$ value, and comparing this value to that determined for all or some of the following related serine proteases: recombinant tissue plasminogen activator (rt-PA), plasmin, activated protein C, chymotrypsin, factor Xa and trypsin. $K_i$ is calculated from the $IC_{50}$.

The buffer used for all assays was HBSA (10 mM HEPES, pH 7.5, 150 mM sodium chloride, 0.1% bovine serum albumin).

The assay for $IC_{50}$ or $K_i$ determinations was conducted by combining in appropriate wells of a Corning microtiter plate, 50 microliters of HBSA, 50 microliters of the test compound at a specified concentration (covering a broad concentration range) diluted in HBSA (or HBSA alone for $V_O$ (uninhibited velocity) measurement), and 50 microliters of the enzyme diluted in HBSA. Following a 30 minute incubation at ambient temperature, 50 microliters of the substrate at the concentrations specified below were added to the wells, yielding a final total volume of 200 microliters. The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value. $K_i$ may be calculated from the $IC_{50}$ value.

Thrombin (fIIa) Assay

Enzyme activity was determined using the chromogenic substrate, Pefachrome t-PA ($CH_3SO_2$-D-hexahydrotyrosine-glycyl-L-Arginine-p-nitroaniline, obtained from Pentapharm Ltd.). The substrate was reconstituted in deionized water prior to use. Purified human a-thrombin was obtained from Enzyme Research Laboratories, Inc. The buffer used for all assays was HBSA (10 mM HEPES, pH 7.5, 150 mM sodium chloride, 0.1% bovine serum albumin).

$IC_{50}$ determinations were conducted where HBSA (50 μL), α-thrombin (50 μl) (the final enzyme concentration is 0.5 nM) and inhibitor (50 μl) (covering a broad concentration range), were combined in appropriate wells and incubated for 30 minutes at room temperature prior to the addition of substrate Pefachrome-t-PA (50 μl) (the final substrate concentration is 250 μM, about 5 times Km). The initial velocity of Pefachrome t-PA hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value. $K_i$ was calculated from the $IC_{50}$ value.

Factor Xa

Factor Xa catalytic activity was determined using the chromogenic substrate S-2765 (N-benzyloxycarbonyl-D-arginine-L-glycine-L-arginine-p-nitroaniline), obtained from DiaPharma Group (Franklin, Ohio). All substrates were reconstituted in deionized water prior to use. The final concentration of S-2765 was 250 μM (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P. *Arch. Biochem. Biophys*. 273:375–388 (1989)]. The enzyme was diluted into HBSA prior to assay in which the final concentration was 0.25 nM.

Recombinant Tissue Plasminogen Activator (rt-PA) Assay rt-PA catalytic activity was determined using the substrate, Pefachrome t-PA ($CH_3SO_2$-D-hexahydrotyrosine-glycyl-Larginine-p-nitroaniline, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2366 [L-pyroglutamyl-L-prolyl-L-arginine-p-nitroaniline hydrochloride], which was obtained from DiaPharma group. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC) Assay aPC catalytic activity was determined using the chromogenic substrate, Pefachrome PC (delta-carbobenzloxy-D-lysine-L-prolyl-L-arginine-p-nitroailine dihydrochloride), obtained from Pentapharm Ltd.). The substrate was made up in deionized water followed by dilution in HBSA prior to the assay in which the final concentration was 400 micromolar (about 3-times Km). Purified human aPC was obtained from Hematologic Technologies, Inc. The enzyme was diluted into HBSA prior to assay in which the final concentration was 1.0 nM.

Chymotrypsin Assay

Chymotrypsin catalytic activity was determined using the chromogenic substrate, S-2586 (methoxy-succinyl-L-arginine-L-prolyl-L-tyrosyl-p-nitroanilide), which was obtained from DiaPharma Group. The substrate was made up in deionized water followed by dilution in HBSA prior to the assay in which the final concentration was 100 micromolar (about 9-times Km). Purified (3×-crystallized; CDI) bovine pancreatic alpha-chymotrypsin was obtained from Worthington Biochemical Corp. The enzyme was reconstituted in deionized water and diluted into HBSA prior to assay in which the final concentration was 0.5 nM.

Trypsin Assay

Trypsin catalytic activity was determined using the chromogenic substrate, S-2222 (benzoyl-L-isoleucine-L-glutamic acid-[gamma-methyl ester]-L-arginine-p-nitroanilide), which was obtained from DiaPharma Group. The substrate was made up in deionized water followed by dilution in HBSA prior to the assay in which the final concentration was 250 micromolar (about 4-times Km). Purified (3×-crystallized; TRL3) bovine pancreatic trypsin was obtained from Worthington Biochemical Corp. The enzyme was reconstituted in deionized water and diluted into HBSA prior to assay in which the final concentration was 0.5 nM.

Table I lists the determined $IC_{50}$ values for certain of the enzymes listed above for compounds of the present invention (depicted in FIGS. 1A and 1B) and demonstrate the high degree of specificity for the inhibition of alpha-thrombin compared to these related serine proteases.

TABLE I

| Compound** | $K_i$ Thrombin* | $IC_{50}$ fxa* | $IC_{50}$ Trypsin* |
|---|---|---|---|
| A | A | I | C |
| B | A | I | I |
| C | A | D | I |
| D | B | I | I |
| E | A | I | I |
| F | A | I | I |
| G | B | I | D |
| H | A | D | D |
| I | A | I | I |
| J | A | I | D |
| K | A | D | I |
| L | A | I | I |
| M | A | I | I |
| N | B | I | I |
| O | B | I | I |
| P | B | D | I |
| Q | C | I | I |
| R | C | I | I |

*
A = ≦100 nM
B = >100, ≦300 nM
C = >300, <2500 nM
D = ≧2500 nM
I = Inactive
**See FIGS. 1A and 1B

We claim:

1. A compound of the formula:

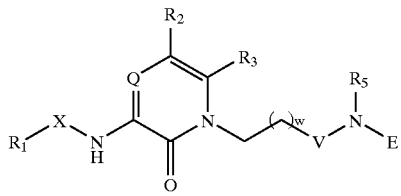

(a) X is selected from the group consisting of —S(O₂)—, —N(R')—S(O)₂, S(O)₂—N(R')—, —C(=O)—, —OC(=O)—, —NHC(=O)—, —C(=O)N(R')—, —P(O)(R')— and a direct link, wherein R' is independently hydrogen, alkyl of 1 to 4 carbon atoms, aryl of 6 to 14 carbon atoms aralkyl of 7 to 16 carbon atoms, with the proviso that when X is —P(O)(R')—, the R' is not hydrogen;

(b) $R_1$ is selected from the group consisting of:

(1) alkyl of 1 to 12 carbon atoms which is optionally substituted with $Y_1$ and/or $Y_2$, (2) alkyl of 1 to 6 carbon atoms substituted with cycloalkyl of 3 to 8 carbon atoms which is optionally mono-, di-, or tri-substituted with $Y_1$, $Y_2$ and/or $Y_3$, (3) cycloalkyl of 3 to 15 carbon atoms, which is optionally mono-, di-, or tri-substituted on the ring with $Y_1$, $Y_2$ and/or $Y_3$, (4) heterocycloalkyl of 4 to 10 ring atoms with the ring atoms selected from carbon and heteroatoms, wherein the heteroatoms are selected from the group consisting of oxygen, nitrogen, and $S(O)_i$, wherein i is 0, 1 or 2, which is optionally mono-, di-, or tri-substituted on the ring with $Y_1$, $Y_2$ and/or $Y_3$, (5) heterocyclo of 4 to 10 ring atoms with the ring atoms selected from carbon and heteroatoms, wherein the heteroatoms are selected from the group consisting of oxygen, nitrogen, and $S(O)_i$, which is optionally mono-, di-, or tri-substituted on the ring carbons with $Y_1$, $Y_2$ and/or $Y_3$, (6) alkenyl of 2 to 6 carbon atoms which is optionally substituted with cycloalkyl of 3 to 8 carbon atoms, which is optionally mono-, di-, or tri-substituted on the ring carbons with $Y_1$, $Y_2$ and/or $Y_3$, (7) aryl of 6 to 14 carbon atoms which is optionally mono-, di- or tri-substituted with $Y_1$, $Y_2$ and/or $Y_3$, (8) heteroaryl of 5 to 14 ring atoms with the ring atoms selected from carbon and heteroatoms, wherein the heteroatoms are selected from oxygen, nitrogen, and sulfur, and which is optionally mono-, di-, or tri-substituted with $Y_1$, $Y_2$ and/or $Y_3$, (9) aralkyl of 7 to 15 carbon atoms which is optionally substituted on the alkyl chain with hydroxy or halogen and which is optionally mono-, di-, or tri-substituted in the aryl ring with $Y_1$, $Y_2$ and/or $Y_3$,

(10) heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and which is optionally mono-, di- or tri-substituted on the ring with $Y_1$, $Y_2$ and/or $Y_3$,

(11) aralkenyl of 8 to 16 carbon atoms which is optionally mono-, di-, or tri-substituted on the aryl ring with $Y_1$, $Y_2$ and/or $Y_3$,

(12) heteroaralkenyl of 5 to 14 ring atoms with the ring atoms selected from carbon and heteroatoms, wherein the heteroatoms are selected from oxygen, nitrogen, and sulfur, and which is optionally mono-, di- or tri-substituted on the ring with $Y_1$, $Y_2$ and/or $Y_3$, (13)

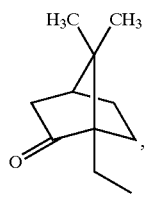

-continued

(14)
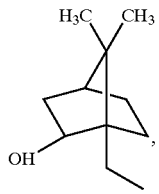

(15)
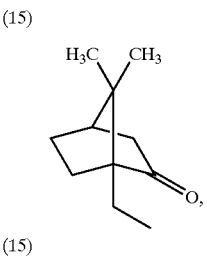

(15)
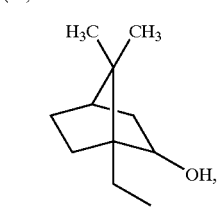

(17) fused carbocyclic alkyl of 5 to 15 carbon atoms,
(18) difluoromethyl or perfluoroalkyl of 1 to 12 carbon atoms,
(19) perfluoroaryl of 6 to 14 carbon atoms,
(20) perfluoraralkyl of 7 to 15 carbon atoms, and
(21) hydrogen when X is a direct link; wherein
  (i) each $Y_1$, $Y_2$ and $Y_3$ is independently selected from the group consisting of halogen, cyano, nitro, tetrazolyl optionally substituted with alkyl of 1 to 6 carbon atoms, guanidino amidino, methylamino, methylguanidino, —$CF_2$, —$CF_2CF_3$, —$CH(CF_3)_2$, —$C(OH)(CF_3)_2$, —$OCF_3$, —$OCF_2CF_3$, —$OCF_2H$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NRC(O)NZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_pZ_1$, —$Z_1$, —$OZ_1$, —$OH$, —$NH_2$, —$NHZ_1$, —$NZ_1Z_2$, N-morpholino, and —$S(O)_p(CF_2)_qCF_3$, wherein p is 0, 1 or 2, q is an integer from 0 to 5, and $Z_1$ and $Z_2$ are independently selected from the group consisting of alkyl of 1 to 12 carbon atoms, aryl of 6 to 14 carbon atoms, heteroaryl of 5 to 14 atoms having 1 to 9 carbon atoms, aralkyl of 7 to 15 carbon atoms, and heteroaralkyl of 5 to 14 ring atoms, or
  (ii) $Y_1$ and $Y_2$ are selected together to be —$O[C(Z_3)(Z_4)]_rO$— or —$O[C(Z_3)(Z_4)]_{r+1}$—, wherein r is an integer from 1 to 4 and $Z_3$ and $Z_4$ are independently selected from the group consisting of hydrogen, alkyl or 1 to 12 carbon atoms, aryl of 6 to 14 carbon atoms, heteroaryl of 5 to 14 ring atoms having 1 to 9 carbon atoms, aralkyl of 7 to 15 carbon atoms, and heteroaralkyl of 5 to 14 ring atoms;
(c) Q is —$C(R_4)$—;
(d) $R_2$ is selected from the group consisting of hydrogen, halogen and alkyl of 1 to 6 carbon atoms;
(e) $R_3$ is selected from the group consisting of hydrogen, alkyl 1 to 6 carbon atoms, cycloalkyl of 3 to 7 carbon atoms, alkoxy of 1 to 6 carbon atoms, halogen, and trifluoromethyl;
(f) alternatively, $R_2$ and $R_3$ are selected together and are —$(CH_2)_k$— where k is 3 or 4;
(g) $R_4$ is selected from the group consisting of hydrogen, alkyl of 1 to 8 carbon atoms, hydroxy, alkoxy of 1 to 8 carbon atoms, aralkyl of 7 to 15 carbon atoms, alkyl of 1 to 5 carbon atoms substituted with cycloalkyl of 3 to 8 carbon atoms, —$NHR_8$, —$S(O)_tR_8$ and —$C(=O)R_8$ where t is 0, 1 or 2;
(h) w is 0, 1 or 2;
(i) V is —$CH(R_5)$—;
(j) $R_5$ is hydrogen or alkyl of 1 to 6 carbon atoms;
(k) E is heteroaryl of 6 to 10 ring atoms having from 1 to 4 ring nitrogen atoms and the remainder of the ring atoms carbon atoms and which is substituted with $R_6$ and $R_7$;
(l) $R_6$ and $R_7$ are independently selected from the group consisting of hydrogen, halogen, hydroxy, alkyl of 1 to 6 carbon atoms, alkoxy of 1 to 6 carbon atoms, alkyl of 1 to 4 carbon atoms substituted with alkoxy of 1 to 4 carbon atoms, trifluoromethyl, —$C(=O)OR_{10}$, —$NHR_{10}$, —$C(=O)R_{10}$, —$C(=O)NHR_{10}$, —$OC(=O)NHR_{10}$, —$C(=NR_{10})NHR_{11}$, and —$N(R_{12})$—$C(=NR_{10})NHR_{11}$; and
(m) $R_8$, $R_9$, $R_{10}$, $R_{11}$ and $R_{12}$ are independently selected from the group consisting of hydrogen, alkyl of 1 to 6 carbon atoms and —$(CF_2)_jCF_3$ wherein j is 0, 1, 2 or 3; or pharmaceutically acceptable salts thereof.

2. A compound according to claim 1 wherein $R_5$ is hydrogen.
3. A compound according to claim 2 wherein X is —$S(O)_2$— or a direct link.
4. A compound according to claim 3 wherein $R_1$ is substituted or unsubstituted aralkyl.
5. A compound according to claim 4 wherein E

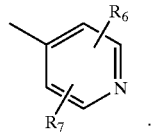

6. A compound according to claim 5 wherein $R_6$ and $R_7$ are independently hydrogen or halogen.
7. A compound according to claim 6 wherein at least one of $R_6$ and $R_7$ is hydrogen.
8. A compound according to claim 7 wherein w is 1.
9. A compound according to claim 7 wherein $R_4$ is hydrogen.
10. A compound according to claim 9 wherein w is 1.
11. A compound according to claim 1 wherein X is —$S(O)_2$—.
12. A compound according to claim 11 wherein $R_9$ is hydrogen or methyl.
13. A compound according to claim 12 wherein $R_1$ is substituted or unsubstituted aralkyl.
14. A compound according to claim 13 wherein $R_9$ is hydrogen.
15. A compound according to claim 14 wherein w is 0 or 1.

16. A compound according to claim 1 wherein E is

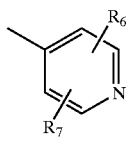

17. A compound according to claim 16 wherein $R_6$ and $R_7$ are independently hydrogen or halogen.

18. A compound according to claim 17 wherein at least one of $R_6$ and $R_7$ is hydrogen.

19. A compound according to claim 18 wherein $R_9$ is hydrogen or methyl.

20. A compound according to claim 1 wherein X is —S(O$_2$)— or a direct link.

21. A compound according to claim 20 wherein $R_1$ is unsubstituted aralkyl, substituted aralkyl or alkyl substituted with cycloalkyl in which the cycloalkyl group is substituted with aryl or heteroaryl.

22. A compound according to claim 21 wherein $R_2$ is hydrogen and $R_3$ is hydrogen or methyl.

23. A compound according to claim 22 wherein $R_3$ is methyl.

24. A compound according to claim 1 selected from the group consisting of Compounds A, B, F, G, H, I, J, K, L, M, N, P, Q and R depicted in FIGS. 1A and 1B.

25. A pharmaceutical composition comprising a pharmaceutically acceptable carrier, and a therapeutically effective amount of compound of claim 1.

26. A pharmaceutical composition comprising a pharmaceutically acceptable carrier, and a therapeutically effective amount of compound of claim 2.

27. A pharmaceutical composition comprising a pharmaceutically acceptable carrier, and a therapeutically effective amount of compound of claim 5.

28. A pharmaceutical composition comprising a pharmaceutically acceptable carrier, and a therapeutically effective amount of compound of claim 12.

29. A pharmaceutical composition comprising a pharmaceutically acceptable carrier, and a therapeutically effective amount of compound of claim 14.

30. A pharmaceutical composition comprising a pharmaceutically acceptable carrier, and a therapeutically effective amount of compound of claim 24.

31. A method for treating a condition in a mammal characterized by thrombosis, comprising administering to said mammal a therapeutically effective amount of the compound of claim 1.

32. A method for treating a condition in a mammal characterized by thrombosis, comprising administering to said mammal a therapeutically effective amount of the compound of claim 2.

33. A method for treating a condition in a mammal characterized by thrombosis, comprising administering to said mammal a therapeutically effective amount of the compound of claim 5.

34. A method for treating a condition in a mammal characterized by thrombosis, comprising administering to said mammal a therapeutically effective amount of the compound of claim 12.

35. A method for treating a condition in a mammal characterized by thrombosis, comprising administering to said mammal a therapeutically effective amount of the compound of claim 14.

36. A method for treating a condition in a mammal characterized by thrombosis, comprising administering to said mammal a therapeutically effective amount of the compound of claim 24.

37. A compound according to claim 12 wherein $R_4$ is hydrogen.

38. A compound according to claim 37 wherein $R_2$ is hydrogen.

39. A compound according to claim 38 wherein $R_3$ is methyl.

40. A compound according to claim 23 wherein $R_4$ is hydrogen.

41. A compound according to claim 1 wherein $R_4$ is hydrogen.

42. A compound according to claim 41 wherein $R_2$ is hydrogen.

43. A compound according to claim 42 wherein $R_3$ is methyl.

44. A pharmaceutical composition comprising a pharmaceutically acceptable carrier and a therapeutically effective amount of a compound of any of claims 1, 2, 5, 12, 14, 24, 40 or 42.

45. A method of treating in a mammal a condition of thrombus formation which comprises administering to said mammal a therapeutically effective amount of a compound of any of claims 1, 2, 5, 12, 14, 24, 40, or 42.

46. A pharmaceutical composition comprising a pharmaceutically acceptable carrier, and a therapeutically effective amount of compound of claim 40.

47. A pharmaceutical composition comprising a pharmaceutically acceptable carrier, and a therapeutically effective amount of compound of claim 42.

48. A method for treating a condition in a mammal characterized by thrombosis, comprising administering to said mammal a therapeutically effective amount of the compound of claim 40.

49. A method for treating a condition in a mammal characterized by thrombosis, comprising administering to said mammal a therapeutically effective amount of the compound of claim 42.

* * * * *